United States Patent [19]

Walker et al.

[11] 4,067,858

[45] Jan. 10, 1978

[54] ACID DERIVATIVE IMMOBILIZED CEPHALOSPORIN CARBOXYLIC CARRYING POLYMER

[75] Inventors: Derek Walker, Windermere; Philip Howard Chapman, Ulverston, both of England

[73] Assignee: Glaxo Laboratories Limited, Greenford, England

[21] Appl. No.: 493,149

[22] Filed: July 30, 1974

[30] Foreign Application Priority Data

July 31, 1973 United Kingdom ............... 36386/73

[51] Int. Cl.$^2$ ............................................. C08G 69/10
[52] U.S. Cl. ........................... 260/78 A; 260/29.6 H; 260/47 UA; 260/47 CZ; 260/78 L; 260/239.1
[58] Field of Search .................. 260/78 A, 260/78 L, 239.1, 29.6 H; 526/19

[56] References Cited

U.S. PATENT DOCUMENTS

| 3,441,526 | 4/1969 | Zilkha et al. ...................... 260/78 A |
| 3,563,958 | 2/1971 | Dorman ............................. 260/78 A |
| 3,743,628 | 7/1973 | Bodanszky et al. ............... 260/78 A |
| 3,775,378 | 11/1973 | Dahlmans et al. ............... 260/78 A |
| 3,784,523 | 1/1974 | Loffet ................................ 260/78 A |
| 3,795,664 | 3/1974 | Tregear et al. .................... 260/78 A |

Primary Examiner—Harold D. Anderson
Attorney, Agent, or Firm—Bacon & Thomas

[57] ABSTRACT

There are provided cephalosporin and penicillin carboxylic acid derivatives which comprise polymers carrying a plurality of molecules of said acid, the carboxyl groups of which are blocked by attachment to the polymer, principally by forming ester linkages to aliphatic carbon atoms in the polymer. There are also provided methods of immobilizing cephalosporin and penicillin acids on polymers and of carrying out chemical reactions to modify said acids.

12 Claims, No Drawings

ACID DERIVATIVE IMMOBILIZED CEPHALOSPORIN CARBOXYLIC CARRYING POLYMER

This invention is particularly concerned with the immobilisation of penicillin and cephalosporin acids and further with the transformation of penicillin and cephalosporin compounds so immobilised.

It is frequently necessary in the manufacture of penicillin and cephalosporin antibiotics to protect the 3- or 4-position carboxyl group, for example by esterification, in order to enable chemical transformations to be carried out elsewhere in the molecule; mild reaction conditions are essential for such esterification and de-esterification processes in view of the facility with which penicillin and cephalosporin compounds may undergo side reactions such as opening of the $\beta$-lactam ring, reaction of the 4-carboxy group of a cephalosporin compound with a 3-substituted methyl group to yield a $\gamma$-lactone derivative, rearrangement of penicillin compounds to anhydro-penicillins or isomerisation of $\Delta^3$-cephalosporin compounds to the corresponding $\Delta^2$-cephalosporins. Various esterifying groups, e.g. groups derived from halo-substituted alkanols or from benzyl alcohol and substituted versions thereof such as diphenylmethanol, have been proposed to fulfill the above mentioned requirements of ease of introduction and subsequent removal.

We have now found that the carboxyl groups of penicillin and cephalosporin acids may be blocked by reaction with certain polymers carrying groups capable of reacting with such carboxyl groups, principally polymers containing ester-forming groups wherein the $\alpha$-carbon atom carries in addition to an ester-forming function a group or groups facilitating subsequent cleavage of the ester linkage. An example of such a polymer esterifying agent is one containing at least one aromatic group attached to the $\alpha$-carbon atom (such polymers hereinafter being referred to as 'aromatic polymer esterifying agents') the esterification reaction yielding novel polymer-bound penicillin and cephalosporin esters wherein the 3- or 4-position carboxyl group of the penicillin or cephalosporin is attached to the polymer through the said $\alpha$-carbon atom. Such polymer-bound protecting groups may be both introduced and subsequently removed in good yield under mild conditions which substantially avoid any degradation of the sensitive penicillin and cephalosporin molecules. We have also found that, in certain cases, penicillins and cephalosporins can be linked, through their carboxyl groups, to polymers by the addition of reagents which activate either the polymer, or the penicillin or cephalosporin.

Polymer esterifying agents and processes for immobilising penicillin and cephalosporin acids on polymers present significant advantages over the previously used monomeric protecting reagents and esterification systems in that the cephalosporin or penicillin molecules are immobilised and transformed on the polymer support and can thus be much more readily separated from unused reagents, by-products and solvents. The utility of polymer-supported synthesis in the transformation of penicillins and cephalosporins is surprising in view of the complexity and sensitivity of the cephalosporins and penicillins and the relative sophistication of the chemical transformations which are of value in this field as compared to the relatively straightforward chemistry of peptide synthesis, the only field in which polymer-supported chemical reactions have been widely employed. It is particularly surprising that complex reactions which have hitherto been conducted only in solution can, in fact, be carried out on a cephalosporin or penicillin substrate which is effectively out of solution; in general longer reaction times are found to be necessary but these rather sensitive molecules nevertheless appear to withstannd much longer contact with reagents surprisingly well and high yields have been obtained in the reactions which have been investigated.

In general, immobilisation of the reactive substrate on a polymer is found to minimise product losses. Thus, for example, a penicillin or cephalosporin substrate bound to a solid polymer may readily be separated from a reaction medium by filtration, centrifugation or decantation in the case of a particulate solid polymer or by simple withdrawal of the medium in cases where the polymer comprises, for example, a formed structure such as a fibrous array or a particulate solid retained in a column, such separations generally being much more convenient and more efficient than conventional separation techniques such as evaporation, precipitation, crystallisation or solvent extraction.

This property of immobilising and retaining substrates renders polymeric carboxyl blocking agents of considerable use in multistage syntheses since the losses which occur in conventional processes in the product isolation step following each stage of the synthesis are substantially obviated when polymer supports are employed.

It will be appreciated that this property is of particular value in the preparation of penicillin and cephalosporin antibiotics, where several reaction stages are generally necessary to obtain a particular antibiotic compound from, for example, a readily available, fermentation-derived penicillin or cephalosporin source material, and that the use of polymer supports as carboxyl blocking groups in such preparations may lead to enhanced yields of penicillin and cephalosporin antibiotics compared to conventional processes using monomeric carboxyl blocking groups.

A further advantage of polymer supported syntheses of penicillins and cephalosporins using polymeric temporary protecting agents concerns the utilisation of all the $\beta$-lactam material. Thus fermenters often produce mixtures of penicillins or mixtures of cephalosporins. In normal batch operations concerned with the transformation of crude mixtures of antibiotics it is usual that at least one component of the mixture is lost in purification operations. This can often represent a substantial loss of desired $\beta$-lactam material, a loss which can frequently be overcome by the use of polymer supports which react with, and hold, all the $\beta$-lactam material. Such a case may be illustrated by pointing to various chemical conversions of crude penicillins G or V, which compounds frequently contain hydroxylated materials, into other products. The hydroxylated material is usually fully utilised in the polymer supported transformations.

In addition to the ease of separating unwanted reagents, byproducts and solvents and the prospect of better overall efficiencies, the use of polymer-supported synthesis techniques offers many major practical advantages. Thus, the elimination of filtration, crystallisation, and drying operations, and the elimination of crystallisation solvents, allows considerable reductions in capital outlay for process and solvent recovery plant as compared with conventional batch process operations. Furthermore, the process simplification afforded by polymer-supported synthesis operations greatly reduces labour and energy requirements, increases the rate of conversion of input material into desired product, and improves the prospects for computer control of a process. In addition the physical standardisation of the chemicals being converted allows considerable flexibility enabling processes with widely differing characteristics to be accommodated in a standard plant.

We have also found to our surprise that polymer-blocked penicillin and cephalosporin acids prepared in accordance with the invention may be employed, with the above-mentioned advantages, as reaction substrates in a wide range of snythetic transformations such as sulphoxidation and desulphoxidation, N-deacylation and reacylation, the ring expansion of penicillin sulphoxides to form cephalosporin compounds, and the transformations of 3-position substituent groups in cephalosporin compounds, eg. by acylation or nucleophilic displacement, using techniques based on those proposed for the transformation of penicillin and cephalosporin compounds protected by conventional monomeric esterifying groups. This finding is unexpected in view of the fact that in reactions such as ring expansions it is well known that the conditions employed are critical for optimal yield, and it is therefore surprising that specific techniques developed for the reaction of monomeric penicillin and cephalosporin esters should prove suitable for the treatment of polymer-bound compounds, particularly since penicillins and cephalosporins protected in accordance with the invention will generally be effectively insolubilised by their being bonded to the polymer support and so might not be expected to react in analogous manner to monomeric penicillin and cephalosporin esters using process techniques developed for reactions in solution.

When aromatic polymer esterifying agents are used in the temporary protection of penicillin and cephalosporin acids in accordance with the invention, these may include aromatic polymer diazomethylenes, hydrazones, alcohols and amines, i.e. polymers wherein the ester-forming groups comprise substituted diazomethylene, hydrazonomethylene, hydroxyalkyl and aminoalkyl groups respectively.

As indicated above, the alphatic $\alpha$-carbon atoms of the ester-forming groups, may each carry at least one aromatic group to facilitate subsequent cleavage of the ester linkages. Examples of suitable aromatic groups include, for example, aromatic hydrocarbon groups having 6 to 10 ring carbon atoms such as phenyl or naphthyl; and substituted versions of any of these groups, for example containing one or more substituents selected from halogen atoms, cyano groups, nitro groups, lower (e.g. $C_{1-6}$) alkyl groups such as methyl, ethyl, n-propyl or isopropyl, and lower alkoxy groups such as methoxy, ethoxy or isopropoxy. In general, particularly when it is desired to cleave the ester group subsequently by acid hydrolysis, we prefer that where the aromatic ring carries substituents these should exhibit electron-donating properties since this facilitates such subsequent cleavage. Preferred substituents therefore include lower alkyl and lower alkoxy groups; thus the use of aromatic polymer esterifying agents containing, for example, mono- or poly-alkoxyphenyl groups such as mono- or poly- methoxy-phenyl attached to the $\alpha$-carbon atoms of the ester-forming groups is of particular value in view of the ease with which subsequent de-esterification may be effected. In general, when aromatic polymer esterifying agents are used, we prefer to employ polymers in which the $\alpha$-carbon atoms of the ester-forming groups are attached through at least two valencies to aromatic groups, since this substitution pattern still further facilitates subsequent cleavage of ester linkages formed by reaction of the polymer and the penicillin or cephalosporin acid.

The $\alpha$-carbon atom of each ester-forming group in an aromatic polymer esterifying agent may form part of the polymer backbone, being bonded through one or, more preferably, two valencies to aromatic groups present in the repeating units of the polymer backbone. In general, however, we prefer to use polymers in which the ester-forming groups form part of side chains attached to the backbone structure; suitable polymers of this type include those in which the $\alpha$-carbon atoms of the ester-forming groups are each attached through one or more valencies to aromatic linking groups, these linking groups themselves being attached to the polymer chain. Suitable linking groups include bivalent analogues of the above-mentioned aromatic groups, for example arylene groups such as phenylene, e.g. p-phenylene. Where the $\alpha$-carbon atoms are attached to such aromatic linking groups through only one valency, they may be bonded through at least one further valency to a hydrogen atom or a substituent atom or group, advantageously an organic substituting group. For the reasons above it is useful to employ polymers in which any organic substituting groups are aromatic groups, but polymers in which the $\alpha$-carbon atoms of the ester-forming groups carry other substituent atoms or groups may also be used, suitable substituents including alkyl groups containing 1-20 carbon atoms, e.g. lower alkyl groups, preferably containing 1-6 carbon atoms, such as methyl, ethyl, n-propyl or isopropyl; cycloalkyl groups, preferably containing 5-7 carbon atoms in the ring, e.g. cyclopentyl or cyclohexyl; aralkyl groups, preferably containing a monocyclic aryl ring and containing 1-6 carbon atoms in the alkyl portion, e.g. benzyl or phenethyl; heterocyclic-substituted alkyl groups, preferably containing an aromatic heterocyclic ring as defined above and containing 1-6 carbon atoms in the alkyl portion, e.g. 2-thienylmethyl, 2-furylmethyl etc.; unsaturated analogues of any of the above groups, e.g. lower alkenyl groups such as vinyl or allyl; cycloalkenyl groups such as cyclohexenyl or cyclopentadienyl, and carbocyclic and heterocyclic aryl-substituted alkenyl; or substituted versions of any of the preceding groups, e.g. groups carrying one or more substituents selected from those listed above as possible substituents for aromatic groups.

In another possibility, the $\alpha$-carbon atoms of the ester-forming groups may each be bonded through one valency to an aromatic group, being attached directly or indirectly through another valency to the polymer chain; again we prefer to use polymers in which the said $\alpha$-carbon atoms are attached through a second valency to aromatic groups linked to or forming part of the polymer chain, so that the $\alpha$-carbon atoms are attached through two valencies to aromatic rings.

Aromatic polymer esterifying agents may be derived from a wide range of polymeric systems, including both solid (at ambient temperature) and liquid homopolymers and copolymers, including cross-linked structures. In general we prefer to use solid polymers in view of the greater facility with which solid polymer-bound substrates may be separated from commonly used reaction systems; solid polymers may be used in particulate form or as preformed structures with or without a mechanical support; suitable preformed structures thus include filaments, films, membranes, tubes, coated wires, coated tubes etc. Particulate and filamentary solid polymers may with advantage be employed in columns.

It will be appreciated that the basic polymer system employed in a given instance should desirably be chemically and physically stable under the conditions in which the polymer esterifying agent and subsequently formed polymer-bound ester derivatives are to be reacted.

One useful class of polymer esterifying agents which may be employed comprises polymers in which the units are derived from styrene or α-methyl-styrene and the α-carbon atoms of the ester-forming groups are attached through one valency to phenyl groups in the repeating styrene units and through the other valency to substituent aryl, e.g. phenyl or methoxylated phenyl groups; advantageously these polymers are cross-linked to a small extent (e.g. 0.1-8%, preferably about 1-2%) by polymerisation in the presence of a cross-linked agent such as divinylbenzene. Styrene polymers, e.g. styrene-divinylbenzene copolymer, are readily available commercially in gel or macroreticular form and may be converted, for instance, to appropriate aromatic polymer esterifying agents by, for example, benzoylation of a proportion of the phenyl rings of the polystyrene and conversion of the keto groups in the resulting benzoylated polystyrene to hydrazonomethylene or diazomethylene groups as described in our British Patent Application No. 36384/73, corresponding to U.S. Pat. 4,038,469 to yield an aromatic polymer hydrazone or diazomethylene, or by benzoylation followed by reduction of the keto groups to hydroxy groups to yield an aromatic polymer alcohol, which polymer alcohol may, if desired, be converted to an aromatic polymer amine, e.g. by conventional techniques such as reaction with a hydrogen halide followed by ammonolysis. A further method of making polymer amines is by reductive amination of a ketopolymer, e.g. by heating the ketopolymer in molten ammonium formate.

Another useful class of polymer esterifying agents is based on polymers of acrylic, methacrylic vinyl ester monomers. Such polymers may be obtained by polymerising acrylic or methacrylic acid ester, amides or nitriles or the free acids themselves and vinyl acetate or vinyl propionate. By copolymerising such monomers with an unfunctionalised monomer such as styrene, the percentage of active ester forming groups in the final polymer can be accurately controlled.

The side chains of such polymers can be converted into ester forming derivatives, for example by first converting such groups to halocarboxyl groups followed by Friedel Craft conversion to aromatic keto groups; the keto group of such polymers may then be converted into groups capable of immobilising cephalosporin and penicillin acids.

Another useful class of polymer esterifying agents are those derived from poly(benzoyl) which may be obtained by oxidation of poly(benzyl) which has the repeating unit ($-CH_2$-phenyl); in this case the esterifying groups form part of the backbone chain of the polymer.

A still further class of useful polymer esterifying agents are those based on polymers of vinyl ketones. Where the vinyl ketones are purely aliphatic, the eventual esterifying groups will be directly attached only to aliphatic groups. Such vinyl ketones can however usefully be copolymerised with aromatic monomers such as styrene.

Although polymeric systems in which the polymer backbone is composed entirely of carbon atoms are preferred by reason of the versatility of polymer esterifying agents prepared therefrom, polymeric systems in which the backbone contains other atoms in addition to carbon, for example oxygen, sulphur and nitrogen, may also be useful. One may thus use, as the polymeric system, a polyester, polyamide or polyurethane. Furthermore, the polymer backbone may be entirely composed of atoms other than carbon such as are frequently found in inorganic polymers. Thus the polymer backbone may contain collections of atoms selected from oxygen, nitrogen, silicon, phosphorus and aluminium. Examples of such systems are polysiloxanes substituted by organic groups for example polymethylphenylsiloxane.

It will be appreciated that the essential characteristic of the polymer esterifying agent is the association of a plurality of esterifying groups with a large supporting molecule. The function of the esterifiable groups is to provide a source of esterifying centres whilst the function of the supporting molecule is simply to provide a structure which provides points of anchorage for the esterifiable groups, and which advantageously is insoluble in the intended reagent systems. Provided the supporting molecule fulfils these requirements and continues to fulfil them during any use of the polymer it can be considered to be a satisfactory polymeric system.

The polymeric system may therefore be chosen according to the envisaged use of the esterifying agent. Thus, while polyesters, polyamides and polyurethanes might all be polymeric systems that are more prone to degradation reactions than polymeric systems in which the polymer backbone is composed entirely of carbon atoms they may all be used satisfactorily provided only that the envisaged use of the polymer esterifying agent is not in a system that may cause degradation of the polymer backbone.

Polymeric systems may be prepared by solution, suspension or emulsion polymerisation and in such polymerisations the reaction will be terminated when the desired molecular weight has been reached. A wide range of molecular weights, in the case of un-cross-linked polymers may be used, for example, up to 500,000, e.g. in the range 200 to 200,000.

When a gel copolymer, e.g. styrene-divinylbenzene, is used in bead form the optimum bead size is dependent on the use to which the polymer esterifying agent is being put. For example, in the case of styrene-2% divinylbenzene copolymer, the best loadings of esterifying groups are usually obtained with polymers of mesh size between 80 and 400, e.g. 80 – 170 and 200 – 400. Such polymers are especially useful in polymer-supported synthesis, particularly in syntheses where intermolecular reactions are not a problem. In those syntheses where intermolecular reactions are a problem lower loadings of esterifying groups can be arranged on the fine mesh size polymers or, alternatively, larger mesh size polymers, e.g. 20–50 may be used. Large mesh size beads are usually more difficult to functionalise to a high loading of reactive groups.

The degree of loading of ester-forming groups on the polymer is preferably comparatively high so that a high loading of penicillin or cephalosporin molecules on the polymer may be obtained, resulting in optimum efficiency as regards use of plant, solvents etc. Thus, for example, where polystyrene-based esterifying agents are used we prefer that at least 20%, preferably at least 30–50% of the polystyrene phenyl rings are substituted by ester-forming groups.

The efficiency of reactions involving either aromatic polymer esterifying agents or polymer-bound penicillin and cephalosporin esters may also be enhanced in many cases by selecting the polymer (e.g. with regard to the degree of cross-linking) and the reaction solvent or solvents employed so that solvent-induced swelling of the polymer occurs, since this will help to expose reactive sites deep in the polymer matrix. In general, solvents which may be employed for this purpose will depend on the nature of the polymeric system and the reactions to be undertaken; useful solvents for the treatment of polystyrenes, for example, include alkanols such as butanol or octanol; N,N-disubstituted amides such as dimethylformamide; aromatic hydrocabons such as benzene or toluene; heterocyclic solvents such as pyridine, tetrahydrofuran or dioxan; halogenated hydrocarbons, e.g. chlorinated aliphatic hydrocarbons such as chloroform or methylene chloride and chlorinated aromatic hydrocarbons such s chlorobenzene; ketones such as methyl ethyl ketone and higher homologues; and esters such as butyl acetate or methyl benzoate. It will be appreciated that the solvent chosen for a particular reaction should be compatible with the reaction system.

Where a polymer diazomethylene is employed as the esterifying agent, esterification of the penicillin or cephalosporin acid may be effected directly under mild conditions, e.g. at room temperature, and in many cases virtually quantitative attachment of the carboxyl groups to the polymer can be achieved with reaction times as short as 5 minutes.

Reaction between a solid polymer diazomethylene and a penicillin or cephalosporin acid is advantageously conducted using an organic solvent, preferably a solvent which promotes swelling of the polymer as described above. Thus the esterification may be effected by, for example, adding a solution of the penicillin or cephalosporin acid in a suitable solvent to a suspension of the polymer, preferably in the same solvent and preferably with agitation. Alternatively the solid penicillin or cephalosporin acid may in some instances be added directly to a slurry of the polymer in a suitable organic solvent, this being of advantage in that, inter alia, solvent requirements are considerably reduced. The penicillin or cephalosporin acid is in general preferably added in slight excess relative to the available diazomethylene groups on the polymer; residual unreacted acid may easily be removed from the reaction solution after separation, e.g. by filtration and washing, of the polymer-bound ester derivative. The course of the esterification may be followed by, for example, monitoring the evolution of nitrogen from the reaction system, this giving a virtually quantitative indication of the extent of the decomposition of diazomethylene groups to from ester linkages, or by monitoring the formation of ester linkages by I.R. spectroscopy. Some indication of the extent of the esterification reaction may be gained from the colour of the reaction system, since aromatic polymer diazomethylenes are normally coloured, this colour weakening or disappearing as the diazomethylene groups are replaced by ester linkages.

If it is desired to use a polymer diazoketone or polymer diazoester as the esterifying agent it is usual to dd a catalyst, e.g. boron trifluoride, a copper salt or p-toluene sulphonic acid. Again it is desirable that the reaction is carried out in an organic solvent which swells the polymer diazomethylene, e.g. a chlorinated hydrocarbon such as chloroform or methylene chloride. The course of the reaction can easily be followed by nitrogen evolution.

Where it is desired to use a polymer hydrazone as the esterifying agent, the esterification should be carried out in the presence of an oxidising agent, for example, an organic peracid such as peracetic acid or m-chloroperbenzoic acid; a system in which peracids are produced in situ e.g. from organic acids and hydrogen peroxide or from ketones such as hexafluoroacetone and hydrogen peroxide; or an N-halosulphonamide (e.g. an N-chloroarylsulphonamide such as chloramine -T or N-chlorosaccharin). Mixtures of oxidising agents, e.g. a combination of a peracid and an N-halo-amide or -imide, may also be used to advantage. Peracetic acid is a particularly preferred oxidising agent. The esterification may be facilitated by the addition of a catalyst, for example a cupric salt such as cupric acetate, a cobalt salt such as cobalt naphthenate, or, more preferably, iodine or an iodide. Esterification reactions of this type between non-polymeric hydrazones and carboxylic acids are described in greater detail in Belgian Patent No. 777898.

Esterifications employing polymer amines are desirably conducted in the presence of a nitrosating agent. Suitable nitrosating agents thus include inorganic nitrosating agents, e.g. nitrosyl derivatives of mineral and Lewis acids, such as nitrosyl chloride, nitrosyl sulphate and netrosyl borofluoride, may also be used.

Reaction between a solid polymer amine and a penicillin or cephalosporin acid is advantageously conducted in the presence of an organic solvent, use of a solvent which swells the polymer again being preferred. Suitable solvents thus include chlorinated hydrocarbons such as methylene chloride or chloroform; aromatic hydrocarbons such as benzene or toluene; heterocyclic solvents such as dioxan; esters such as butyl acetate; ketones such as methyl ethyl ketone; N,N-disubstituted amides such as dimethylformamide; and alcohols such as butanol (alcohols react with nitrosyl chloride and should preferably not be used with this nitrosating agent).

The esterification is conveniently effected at a temperature in the range $-50°$ to $+100°$ C, e.g. $-30°$ to $+20°$ C. The esterification may again conveniently be monitored by measuring the volume of nitrogen evolved as the reaction proceeds.

Reaction of penicillin and cephalosporin acids with polymer alcohols may be effected using any convenient technique. One suitable method comprises reaction in the presence of at least one mole of a compound which forms a reactive derivative with either the carboxyl or hydroxyl groups such as phosphorus oxychloride or p-toluene sulphonyl chloride to promote the ester-forming reaction; it may be advantageous to activate the polymer by treatment with such a compound prior to addition of the penicillin or cephalosporin acid to be esterified. When a polymer alcohol is used with, for example, phosphorus oxychloride the reaction is preferably conducted in the presence of an acid binding agent, e.g. a tertiary amine, conveniently a heterocyclic nitrogen base such as pyridine or quinoline. Alternatively the esterification may be conducted in the presence of a condensing agent, for example a carbodiimide such as dicyclohexylcarbodiimide. A further useful technique comprises reaction of the polymer alcohol with a penicillin or cephalosporin acid activated at the carboxyl group, for example by formation of an appropriate anhydride, e.g. a mixed anhydride such as one derived from acetic acid, or formation of an active ester, e.g. a p-nitrophenyl ester. Methods for the preparation of such activated derivatives of cephalosporin and penicillin acids are well-known in the art.

We again prefer to conduct the esterification in an organic solvent, particularly a solvent which swells the polymer alcohol, the use of halogenated hydrocarbons such as methylene chloride being convenient in this respect. The course of the esterification may be monitored by, for example, I.R. spectroscopy.

In general, a good indication of the overall extent of the esterification reaction may be obtained by determining the total gain in weight of the polymer during the esterification.

Polymer esterifying agents may be used in the temporary protection of a wide range of penicillin and cephalosporin acids, including naturally occuring fermentation-derived compounds such as penicillin G, penicillin V and cephalosporin C, as well as synthetic and semisynthetic penicillins and cephalosporins related thereto or derived therefrom, including their sulphoxide derivatives.

Where it is desired to temporarily protect the carboxyl groups of cephalosporin C it is usually necessary to block the free amino group in the amino-adipoyl side chain, e.g. by protonation or acylation.

An indicated above, polymer-bound penicillin and cephalosporin esters may be used as reaction substrates in a wide range of transformation reactions.

Thus, for example, polymer-bound penicillin and cephalosporin sulphide esters may be oxidised to the corresponding sulphoxide by, for example, treatment with a peracid, preferably an organic peracid and particularly peracetic acid, or with a periodate, e.g. sodium metaperiodate. The oxidation is advantageously carried out in the presence of an organic solvent, preferably a solvent such as chloroform or methylene chloride which swells the polymer support, at a temperature not exceeding 50° C, e.g. in the range $-10°$ to $+15°$ C. The sulphoxidation may if desired, be combined with an oxidative esterification reaction, e.g. employing an aromatic polymer hydrazone.

Similarly, polymer-bound sulphoxides may be reduced to the corresponding sulphide, e.g. by treatment with a phosphorus trihalide or a dialkyldithiophosphoric acid in a solvent such as methylene chloride or dimethylformamide; reduction may also be effected by treatment of an acyloxysulphonium or alkyloxysulphonium salt derived from the sulphoxide with sodium dithionite or an iodide salt.

Polymer-bound penicillins and cephalosporins may be N-deacylated using standard techniques, e.g. imide halide techniques analogous to those described in British Patent Nos. 1,041,985; 1,110,806; 1,189,022; 1,227,014; 1,239,814; 1,241,655 and 1,244,191. Thus, for example, a polymer-bound ester of a (3S, 5R, 6R)-6-acylamido-2,2-dimethylpenam-3-carboxylic acid such as penicillin G or penicillin V or a (6R, 7R)-7-acylamido-3-methylceph-3-em-4-carboxylic acid may be converted to a polymer-bound ester of (3S, 5R, 6R)-6-amino-2,2-dimethylpenam-3-carboxylic acid (6-APA) or (6R, 7R)-7-amino-3-methylceph-3-em-4-carboxylic acid (7-ADCA) respectively by treatment with an aimide halide-forming reagent such as phosphorus pentachloride (which may be formed in situ from phosphorus trichloride and chlorine) or phosgene in the presence of a suitable solvent, e.g. a chlorinated hydrocarbon such as methylene chloride and in the presence of a tertiary organic amine such as pyridine or dimethylaniline; if desired separating and washing the resulting polymer-bound imide halide, e.g. with methylene chloride; converting the polymer-bound imide halide into an imino ether by treatment with an alcohol, e.g. a lower alkanol such as methanol or a diol such as butane-1,3-diol, if desired in the presence of a swelling solvent such as methylene chloride, and cleaving the imino ether group. The desired cleavage of the imino ether group may in some instances take place during the reaction with the alcohol; in other cases, however, a separate hydrolysis or alcoholysis step may be necessary to promote this cleavage, and may be achieved by, for example, treating the polymer with water or methanol, advantageously under acidic conditions (which will often result from previous stages).

The imide halide-forming reagent is conveniently used in excess, although large excesses (e.g. greater than a 10 molar excess) tend to be uneconomical, and we therefore prefer to employ about 1-3 moles, e.g. about 1.5 moles, of, for example, phosphorous pentachloride per mole of polymer-bound penicillin or cephalosporin compound. The base is conveniently used in substantially equivalent amounts to the quantity of imide halide-forming reagent employed. The temperature for the reaction of the imide halide-forming reagent may be, for example, in the range $-50°$ to $+50°$ C, e.g. $-10°$ to $+30°$ C; the optimum temperature will depend, to some extent at least, on the reactants employed.

The alcohol employed in the imino ether-forming step may be used in substantial excess, e.g. up to 75 moles and possibly even 100 moles over the polymer-bound penicillin or cephalosporin compound. The reaction temperature for this step may, for example, be in the range $-50°$ to $+30°$ C, e.g. $-30°$ to $+20°$ C, the optimum temperature being readily determinable by experiment.

Where a separate imino ether-cleavage step is necessary, this is conveniently effected by the addition of, for example, water or methanol, e.g. at $-5°$ to $+20°$ C, it having been ensured that the preceding steps were so carried out that acid is present in the reaction system. If necessary, however, further acid, e.g. a mineral acid such as hydrochloric acid, sulphuric acid, nitric acid or phosphoric acid, or an organic acid such as p-toluenesulphonic acid or formic acid may be added.

Extended reaction times may be necessary in the various steps of the N-deacylation process to give optimum yields, owing to the need for the reagents to diffuse through the structure of the polymer support.

The fact that polymer-bound penicillins and cephalosporins may be N-deacylated in this may, using imide halide techniques substantially analogous to those previously described for the N-deacylation of monomeric penicillin and cephalosporin esters, is most unexpected in view of the limitations imposed by the structure of the polymer support on the rate of diffusion of reagents to the sites of the 6- or 7-position amido groups and the known requirement that successful N-deacylation of penicillin and cephalosporin is critically dependent on the reaction conditions. Indeed, as far as we are aware, no amide cleavage using the imide halide technique has ever been accomplished on an amide which is insoluble in the reaction solvent.

In the particulr case of polymer-bound cephalosporins the N-deacylation reaction may be combined with an advantageous functionalisation of the 3-position. Thus, a polymer-bound 3-hydroxymethyl cephalosporin may be subjected to the above described N-deacylation to yield, on the polymer, a 3-halomethyl-7-amino cephalosporin which may then be subjected to desired manipulations at the 7- and 3-positions.

N-deacylated polymer-bound penicillin and cephalosporins may be reacylated using a wide range of conventional techniques well known in the penicillin and cephalosporin art to form any of the very large number of 6- and 7-acylamido groups proposed in connection with the preparation of penicillin and cephalosporin antibiotics.

In general, the acyl group introduced will contain 1–20 carbon atoms. One preferred class of acyl groups comprises substituted acetyl groups in which the α-carbon atom is additionally substituted by an amino group, examples of such groups including R-α-aminophenylacetyl and R-α-aminocyclohexadienylacetyl. The former of these groups is of course the acyl portion of the 6- and 7-side chains respectively of the important antibiotics ampicillin and cephalexin, while the latter is the acyl portion of the 7-position side chain of dihydrocephalexin.

The acylation may be effected with any convenient acylation agent such as, for example, an acid halide (e.g. chloride or bromide), an anhydride or mixed anydride, e.g. with pivalic acid or formed with a haloformate, e.g. a lower alkylhaloformate or an active ester or azide; alternatively, the acid itself can be used, together with a dehydrating agent, e.g. carbonyldiimidazole or a carbodiimide such as N,N'-diethyl-, dipropyl-, or diisopropylcarbodiimide, or, more preferably, N,N'-dicyclohexylcarbodiimide. The acylation may be carried out in a solvent medium with an acid halide, preferably in the presence of an acid-binding agent. Suitable solvents include halogenated hydrocarbons (e.g. dichloromethane), ketones (e.g. methyl isobutyl kentone), cyclic ethers (e.g. dioxan or tetrahydrofuran) or esters (e.g. butyl acetate). Suitable acid-binding agents include tertiary amines such as triethylamine, pyridine or dimethylaniline; and inorganic basis such as calcium carbonate or sodium bicarbonate.

One convenient method of performing the N-acylation step is to employ an acyl halide (such as described above) in the presence of an oxirane, e.g. a moni- or di-epoxide, preferably a lower 1,2-alkylene oxide such as propylene or ethylene oxide, which itself acts as an acid-binding agent for acid liberated in the reaction. The reaction medium may be the oxirane itself or an organic solvent of the type referred to in the last but one paragraph. A reaction temperature of, for example, 0° to +50° C may be used.

Alternatively, the acylation may be effected with an acid halide or mixed anhydride under substantially anhydrous conditions in the presence of an inert Lewis base (preferably one having a tertiary nitrogen atom) having a dielectric constant above 15 and preferably above 30 and containing a hydrogen halide acceptor. The halide is advantageously the chloride or bromide. This method is described in British Pat. No. 1,104,937.

When the acylating reagent contains an amino group it is necessary to protect it during the acylation. The protecting group should of course be one which can be removed without affecting the rest of the molecule, especially the lactam and 7R-amido linkages. Many such protecting groups are known. Removal of the amine protecting group and cleavage of the penicillin or cephalosporin from the polymer support may in some cases be effected using the same reagent normally as the last stage of a reaction sequence. Types of protected amino groups and examples thereof or of reagents used in their formation are illustrated in the following Table:

| Type | Protecting Group (or reagent used) |
|---|---|
| Urethane | Benzyloxycarbonyl, p-Methoxy benzyloxycarbonyl |
| Urethane | t-Butoxycarbonyl |
| Urethane | Diphenylmethoxycarbonyl |
| Urethane | 1-Adamantyloxycarbonyl |
| Urethane | β,β,β-trichloroethoxycarbonyl |
| Arylmethyl | Trityl |
| Sulphenyl | o-Nitrophenylsulphenyl, p-nitro- |
| Enamine | Ethyl acetoacetate Acetylacetone Benzoylacetone Methyl acetoacetate Propionylacetone |
| Arylmethylene | 5-chlorosalicylaldehyde 3,5-dichlorosalicylaldehyde 2-hydroxy-1-naphthaldehyde 3-hydroxy-pyridine-4-aldehyde |

Such groups can be removed in known manner appropriate to the groups concerned e.g. by treatment with dilute mineral or organic acids, or liquid hydrogen bromide at very low temperature, e.g. $-80°$ C. One useful protecting group is the t-butoxycarbonyl group, which is readily removed selectively; i.e. without cleaving polymer ester groups, when hydrogen chloride in a cyclic ether such as dioxan; less selective cleavage, which may be used simultaneously to remove the cephalosporin or penicillin from the polymer may be effected by hydrolysis with dilute aqueous mineral acid, e.g. dilute hydrochloric acid, or more preferably, with a strong acid (e.g. formic acid, trifluoroacetic acid or liquid HF), e.g. at a temperature of 0°–40° C, preferably at room temperature (15°–20° C). Another protecting group is the 2,2,2-trichloroethoxycarbonyl group which may be split off by reduction, e.g. using a zinc/acid system such as zinc/acetic acid, zinc/formic acid, zinc/lower alcohols or zinc/pyridine, after cleavage of the penicillin or cephalosporin from the polymer support. Polymer-bound cephalosporin compounds may also be reacted to transform a substituent at the 3-position. Thus one may effect a nucleophilic displacement of the acetoxy portion of a 3-acetoxymethyl compound by methods similar to those described in British Patents Nos. 912,541; 1,012,943; 1,030,630; 1,059,562; 1,082,943; 1,082,962; 1,101,423 or 1,206,305. Alternatively nucleophilic displacements may be effected on a 3-halomethyl compound as described in British Patents Nos. 1,241,657 and 1,326,531. Such 3-halomethyl compounds may be prepared from the corresponding 3-hydroxymethyl compounds by reaction with a halogenating agent such as thionyl chloride as described - British Pat. No. 1.242.658. Other 3-substituted methyl compounds may be produced from 3-hydroxymethyl compounds thus, for example, 3-acyloxymethyl compounds may be produced by acylation of a 3-hydroxymethyl compound as described in British Pat. No. 1,141,293.

Compounds possessing a 3-carbamoyloxy methyl group may also be prepared from 3-hydroxymethyl compounds. However, in this case, the starting material is reacted with an isocyanate of formula $R^2.NCO$ (wherein $R^2$ represents a labile substituent group) to give a compound containing a precursor group of formula -CH$_2$O.CO.NHR$^2$ (where R$^2$ has the above defined meaning) at the 3-position. Such precursor groups may be converted to the desired 3-carbamoyloxymethyl group by subsequent cleavage of the group R$^2$, e.g. by hydrolysis. Labile groups R$^2$ which are readily cleavable upon such subsequent treatment include chlorosulphonyl and bromosulphonyl (see German OLS 2,203,653); aralkyl groups such benzyl, p-methoxybenzyl and diphenylmethyl; lower alkyl groups such as t-butyl: and halogenated lower alkanoyl groups such as trichloroacetyl.

3-Hydroxymethyl starting materials for use in the above process embodiment of the invention may be prepared by, for example, the methods described in British Patent No. 1,121,308.

The success of reactions which involve displacement of 3-position substituents on polymer-bound and thus insolubilised cephalosporins is both unexpected and unprecedented.

One particularly important transformation is the ring expansion of penicillin sulphoxides immobilised through the carboxyl group, i.e. as esters, on an insoluble polymer support to yield polymer supported Δ$^3$-3-methyl cephalosporin esters. This transformation is particularly applicable to sulphoxides of fermentation-produced penicillins such as penicillin G and penicillin V. Such ring expansion reactions using conventional ester derivatives are of great importance in the industrial production of cephalosporin antibiotics such as cephalexin and a variety of reaction conditions which promote such ring expansions have been proposed. These generally involve heating the penicillin sulphoxide ester in an organic solvent in the presence of a catalyst, suitable catalyst and solvent systems being described in, for example, our British Patent Specifications Nos. 1,299,734; 1,312,232 and 1,312,233. To our surprise we have now found that penicillin sulphoxide esters in which the ester moiety is derived from a polymer esterifying agent in accordance with the invention may be ring expanded to the corresponding Δ$^3$-3-methyl cephalosporin esters in high yield, the process being rendered particularly convenient by the efficient separations, reduced solvent requirements, reduction in product losses and improved opportunities for recovering the catalyst which accrue from the use of a polymer support.

While we do not wish to be bound by theoretical considerations it is known that ring expansion reactions proceed better at high dilutions, presumably because of the reduction of intermolecular interactions. Highly dilute reaction solutions are undesirable where conventional ester derivatives are reacted since the cost of suitable solvents such as dioxan is high, and subsequent separation of the cephalosporin product is somewhat complicated. In polymer-bound ester systems, however, the comparatively wide spacing between polymer-attached penicillin molecules and the substantially fixed bonding of these molecules to the polymer markedly reduces the possibility of intermolecular interactions so that the ring expansion of the polymer-bound penicillin sulphoxides is effectively carried out under circumstances which approach infinite dilution conditions.

Ring expansion of a polymer-bound penicillin sulphoxide may be effected by heating a suspension of the polymer-bound material in an organic solvent, preferably under reflux, in the presence of a catalyst, catalysts and solvents for this purpose including those described in our above-mentioned British Patent Specifications Nos. 1,299,734; 1,312,232 and 1,312,233.

One preferred ring expansion technique of this sort comprises refluxing a suspension of the polymer-bound penicillin sulphoxide in an inert solvent, especially dioxan, in the presence of a salt of an organic amine having a pKb of not less than 4 (preferably a heterocyclic tertiary amine such as pyridine) and an acid (preferably orthophosphoric acid or a phosphonic acid such as dichloromethane phosphonic acid or m-nitrobenzene phosphonic acid), which salt may be formed in situ in the reaction mixture. In another preferred method, the rearrangement is carried out in the presence of a mono-O-substituted or O,O-di(aryl-substituted) orthophosphoric acid or a salt thereof with an organic amine having a pKb of not less than 4 (preferably a heterocyclic tertiary amine such as pyridine), which salt may again be formed in situ, the reaction preferably being conducted under reflux in an inert solvent such as dioxan.

A particularly preferred embodiment of this latter method comprises refluxing a suspension of the polymer-bound penicillin sulphoxide in dioxan in the presence of pyridinium 2,2,2-trichloroethyl dihydrogen phosphate, which is conveniently formed in situ in the reaction system from pyridine and 2,2,2-trichloroethyl dihydrogen phosphoric acid.

Other ring expansion techniques which may be used include that described in U.S. Pat. No. 3,647,787, this involving heating the penicillin sulphoxide ester under acid conditions in a tertiary carboxyamide, tertiary urea or tertiary sulphonamide solvent medium, and the development thereof described in U.S. Pat. No. 3,591,585 wherein the rearrangement is effected using a tertiary carboxyamide - containing solvent in the presence of a sulphonic acid and steps are taken to remove or inactivate any water present.

It is generally of advantage in ring expansion reactions to remove water formed during the reaction, for example by azeotropic drying or by continuously passing the solvent over a drying agent such as sodium hydroxide.

The course of the ring expansion may be monitored by, for example, I.R. spectroscopy, e.g. by following the shifts in the amide, β-lactam and ester carbonyl absorptions which accompany conversion of a penicillin compound to a cephalosporin.

As indicated above, the ease with which polymer-bound penicillins and cephalosporins may be separated from a particular reaction medium and residual traces of the reaction medium removed from the polymer, e.g. by washing, coupled with the negligible losses of product occurring in such separation procedures, render the use of polymer-bound protecting groups of particular value in multi-stage processes, such as the conversion of fermentation-derived penicillins and cephalosporins to more potent semisynthetic antibiotic compounds. Thus, for example, a polymer-bound ester of a penicillin such as penicillin G or penicillin V may be subjected to a reaction sequence involving N-deacylation, e.g. by the above-described imide halide technique, and subsequent reacylation, e.g. with an N-protected derivative of R-aminophenylacetyl chloride, to yield (after any deprotection reaction which may be necessary) a polymer-bound penicillin antibiotic. Alternatively the polymer-bound penicillin starting material may be subjected sequentially to oxidation to form the corresponding sulphoxide, ring expansion to form a polymer-bound $\Delta^3$-3-methyl cephalosporin and N-deacylation to yield a polymer ester of the commercially important intermediate 7-ADCA (which may if desired be reacylated, e.g. by treatment with 2- N-2,2,2-trichloroethoxycarbonyl-amino 2-phenylacetyl chloride or the mixed anhydride derived from ethyl chloroformate and N-t-butoxycarbonyl-2-amino-2-phenylacetic acid to yield an N-blocked polymer ester of the important antibiotic, cephalexin, prior to removal from the polymer.)

In the particular case of reactions involving polymer hydrazones we have found that the desired polymer-bound penicillin sulphoxide may be obtained from a penicillin sulphide and a polymer hydrazone directly. The reagents are contacted to the presence of an oxidising agent and the polymer-bound penicillin sulphoxide is obtained. While After the desired transformations of the polymer-bound penicillin or cephalosporin compound have been effected, the resulting compound may be liberated from the polymer by, for example, cleavage of the ester linkages with acid or by reductive methods in such a way as to minimise decomposition of the desired penicillin or cephalosporin. In general we prefer to use cleavage with acid for example, or a solution of a mineral acid such as hydrochloric acid, an organic acid such as trifluoroacetic acid, formic acid or a Lewis acid such as boron trifluoride in a substantially non-aqueous solvent such as acetic acid, chloroform or dioxan, solvents which promote swelling of the polymer again being preferred. Trifluoroacetic acid in chloroform is a particularly convenient reagent for the hydrolytic cleavage of a range of polymer-bound esters.

A preferred method for the cleavage of polymer-bound esters employs a combination of formic acid and a sulphonic acid, e.g. p-toluenesulphonic acid, in a solvent which swells the polymer e.g. methylene chloride or chloroform. In this process the sulphonic acid need be present in relatively small amount, e.g. in amount of from 0.1 to 3 moles with respect to the cephalosporin on the polymer.

After the de-esterification reaction the polymer may be removed from the system by, for example, filtration and the liberated carboxylic acid separated from the filtrate by, for example, conventional methods such as solvent evaporation and/or crystallisation.

The polymer remaining after cleavage of the ester linkages will normally be a polymer ester or alcohol. If desired, this material may be oxidised to the corresponding polymer ketone, for example by treatment with nitric acid, with chromium trioxide in acetic acid or with aluminium-t-butoxide in cyclohexanone or methyl isobutyl ketone and the resulting keto groups converted to diazomethylene groups as described in our copending Application No. 36384/73, or may be reused directly as an esterifying agent, e.g. in the presence of phosphorus oxychloride.

The following non-limitative Examples serve to illustrate the invention. All temperatures are in ° C.

Proton magnetic resonance spectra were recorded on a Varian A60 model. Signs of the coupling constants are not indicated. Spectra run from polymeric samples were generally conducted by taking 100 mgs of polymer in c.a. 1 ml. of a 2:1 mixture of $CDCl_3$ and Trimfluoroacetic acid and running the spectrum on either the resulting slurry or, more usually, on the filtrate after removal of the polymer.

Thin layer Chromatography was conducted on Merck silica-gel coated plates. Optical rotations were measured with a Hilger and Watts Mk. III polarimeter calibrated with sucrose $[\alpha]_D^{20} + 66.5°$ (c. 0.26 in water).

IR spectra were determined on a Perkin Elmer model 257, either as Nujol Mulls or KBr Discs.

Nitrogen volumes are uncorrected.

PREPARATION OF STARTING MATERIALS a. Benzoylated Styrene - 2% divinylbenzene Copolymer Resin Styrene - 2% divinylbenzene copolymer gel [Eastman Organic Chemicals, Kodak Catalogue 46 (26th March 1971), Catalogue No. 11180] (200 - 400 mesh, 30.0g) was suspended in dry carbon disulphide (180 ml.) at room temperature. To the stirred suspension were added powdered anhydrous aluminium chloride (8.4g., $0.30 \times 10^{-2}$ moles) and benzoyl chloride (7.0 ml., $6.03 \times 10^{-2}$ moles) and the mixture stirred at room temperature for 15 minutes and then heated under reflux for 2½ hours. Carbon disulphide (ca. 100 ml.) was removed from the reaction mixture by distillation to leave a dark-brown slurry. After cooling to 5° the stirred slurry was treated with cold 50% aqueous hydrochloric acid (100 ml.). After stirring at room temperature for 30 minutes the product was collected by filtration; successively washed with 50% aqueous hydrochloric acid (100 ml.), water (2 × 100 ml.) and methanol (2 × 100 ml.); and dried at vacuo at 38° overnight. The resin (34.85g.) was pale yellow in colour and the IR spectrum exhibited a characteristic carbonyl absorption at 1661 $cm^{-1}$.

b. Hydrazone of Benzoylated Styrene - 2% divinylbenzene Copolymer Resin

Benzoylated styrene - 2% divinylbenzene copolymer resin 34.75%) from Example (a) was suspended in butan-1-ol (300 ml.), the stirred suspension treated with 99% hydrazine hydrate (30.0 ml., 0.61 mole) and the mixture heated under reflux with stirring for 24 hours. After cooling the product was filtered, washed with butan-1-ol (3 × 50 ml.) and dried in vacuo at 38° overnight. The product (35.45g) was off-white in colour and the IR spectrum exhibited absorptions at 3410 $cm^{-1}$ (=N — $NH_2$) and 1657 $cm^{-1}$ (—C = N—).

c. Polymer Diazomethylene from the Hydrazone of Benzoylated Styrene - 2% divinylbenzene Copolymer Resin The polymer hydrazone of (b) above (35.35g.) was suspended in methylene chloride (250 ml.) and treated with 1,1,3,3-tetramethylguanidine (21.0 ml., 0.167 mole) followed by a 1% solution of iodine in methylene chloride (1.0 ml., $2.54 \times 10^{-5}$ mole) and the mixture cooled to $-10°$. Peracetic acid (11.9 ml., $6.74 \times 10^{-2}$ mole, 38% w/w in glacial acetic acid) was then added dropwise over 15 minutes to the stirred suspension while the temperature of the reaction was maintained between $-5°$ and $-10°$. Reaction was accompanied by an immediate colour change from white to deep magenta. After addition was complete the mixture was stirred for a further 30 minutes at 0° and then filtered. The product was washed with methylene chloride (2 × 50 ml.) and dried in vacuo at 30° overnight. The resin (34.24g.) was deep magenta in colour and the IR spectrum exhibited the characteristic diazoalkane absorption at 2038 $cm^{-1}$.

EXAMPLE 1 a. Polymer Ester of (1s,3,S,5R,6R)-2,2-Dimethyl-6-phenylacetamidopenam-3-carboxylic Acid 1-Oxide Styrene - 2% divinylbenzene Copolymer A stirred slurry of a styrene - 2% divinylbenzene copolymer-based diazomethylene prepared as described above (60.0g) in chloroform (300 ml. containing 2% v/v ethanol) at room temperature was treated dropwise over 30 minutes with a solution of penicillin G sulphoxide acid acetone solvate (50.0g, 0.122 mole) in chloroform (350 ml. containing 2% v/v ethanol. Effervescence caused by nitrogen evolution occurred, accompanied by decolourisation of the magenta polymer diazoalkane and a 7° temperature rise. After the addition was complete the magenta colour had faded completely to a pale yellow colour. The mixture was stirred for a further 30 minutes to ensure complete reaction and then the product was filtered, washed with chloroform (2 × 200 ml. slurry wash, 2 × 200 ml. displacement wash), and dried in vacuo at 36° to yield the pale yellow title product (87.0g); $\nu$ max (Nujol) 3380 (—HN—CO—), 1800 ($\beta$-lactam), 1750 (ester carbonyl), 1665 and 1497 cm$^{-1}$ (amidecarbonyl). Excess starting material was recovered by evaporating the chloroform filtrate and washings under reduced pressure and triturating the residue with dry acetone (50 ml.), which afforded, after filtration and drying, penicillin G sulphoxide acid acetone solvate (19.55g, 0.048 mole) identical in all respects with an authentic sample.

b. Polymer Ester of 6R,7R)-3-Methyl-7-phenylacetamidoceph-3-em-4-carboxylic Acid The polymer ester of Example 1(a) (87.0g) and mono (2,2,2-trichloroethyl) phosphate (1,30g) were heated under reflux in dioxan (450 ml.) containing pyridine (0.45 ml.) for 30 hours, the solvent being passed continuously through sodium hydroxide pellets during this period. The mixture was cooled and the resin filtered, washed with dioxan (2 × 100 ml.) and dried in vacuo at 38° to give the dark brown title product (86.9g); $\nu$ max. (Nujol) 3290 (—NH—CO—), 1775 ($\beta$-lactam), 1720 (ester carbonyl), 1656 and 1490 cm$^{-1}$ (amide carbonyl). The nature of this product is confirmed by the following Example.

c. (6R,7R)-3-Methyl-7-phenylacetamidoceph-3-em-4-carboxylic Acid

A sample of the polymer product of Example 1 (b) (1,0g) in chloroform (5.0 ml.) and trifluoroacetic acid (5.0 ml.) was stirred at room temperature for 1 hour. The residual polymer was removed by filtration and washed with chloroform. Thin layer chromatography of the filtrate was carried out on silica gel, eluting with butyl acetate (80), water (40), acetic acid (24), butan-1-ol (15) and methanol (5) and spot location was determined by UV irradiation and then spraying the heated plate with tetrazolium blue. This indicated the presence of (6R,7R)-3-methyl-7-phenylacetamidoceph-3-em-4-carboxylic acid as a single spot material (Rf 0.53) identical with an authenic specimen.

EXAMPLE 2 a. Polymer Ester of (6R,7R)-7-Amino-3-methylceph-3-em-4-carboxylic Acid

Pyridine (4.88 ml., 0.061 mole) was added over 5 minutes to a stirred suspension of phosphorus pentachloride (12.59g, 0.061 mole) in methylene chloride (100 ml.) and the mixture stirred at 25° - 30° for 25 minutes and then cooled to −10°. The polymer ester of Example 1 (b) (30.0g) was then added and washed in with methylene chloride (100 ml.). The dark brown slurry was stirred at 15° - 20° for 2 hours, cooled to −10° and treated with a cold mixture of butane-1, 3-diol (100 ml.) in methylene chloride (100 ml.) such that the temperature did not rise above −5°. The brown suspension was stirred at −5° for 30 minutes, cooled to −15° and treated with water (100 ml.) and the mixture stirred at 0° for 1 hour. The resin was filtered and washed successively with methylene chloride (50 ml.), methanol (50 ml.), water (50 ml.), and methanol (2 × 50 ml.) and dried in vacuo at 38° overnight. The ginger title product (26.6g) so obtained exhibited $\nu$ max (Nujol) 3170 (NH$_2$), 1795 ($\beta$-lactam) and 1720 (ester carbonyl), the nature of this product being confirmed by the following Example.

b. (6R,7R)-7-Amino-3-methylceph-3-em-4-carboxylic Acid

The polymer product of Example 2(a) (26.6g) in chloroform (80 ml.) and trifluoroacetic acid (50 ml.) was stirred at room temperature for 1 hour. The residual polymer was removed by filtration and washed with chloroform (100 ml.). Thin layer chromatography of the filtrate was carried out on silica gel eluting with butyl acetate (80), water (40), acetic acid (24), butan-1-ol (15) and methanol (5) and spot location was determined by UV irradiation and then spraying the plate with 0.5% solution of ninhydrin in butan-1-ol followed by warming. This indicated the filtrate to contain (6R,7R)-7-amino-3-methylceph-3-em-4-carboxylic acid (yellow spot Rf 0.04) together with lesser amounts of faster moving material. The filtrate and washings were evaporated under reduced pressure and the residue triturated with diethyl ether (50 ml.) and cooled. Crude (6R,7R)-7-amino-3-methylceph-3-em-4-carboxylic acid (5.03g) was recovered as a buff solid whose IR spectrum resembled strongly that of an authentic sample. The crude product was dissolved in 5% aqueous ammonia and stirred with charcoal for 30 minutes. After filtration the filtrate was brought to pH 4.0 with concentrated hydrochloric acid and the solid collected and dried to afford (6R,7R)-7-amino-3-methylceph-3-em-4-carboxylic acid (3.52g, 70.0%) as an off-white solid. Thin-layer chromatography, as above, indicated the product to be single spot material. IR and NMR spectra were identical with those of an authentic sample. $[\alpha]_D^{20}$ 153° (c0.5 in 0.2M, pH 7.0 phosphate buffer).

EXAMPLE 3

Polymer Ester of (1S, 3S, 5R, 6R)-2,2-Dimethyl-6-Phenylacetamidopenam-3Carboxylic Acid 1-Oxide via Amine Nitrosation A solution of penicillin G sulphoxide acetone solvate (0.5g., 1.22 × 10$^{-3}$ mole) in methylene chloride (25 ml.) was added to a stirred slurry of benzhydrylamine polymer [5.0g., containing 1.20 × 10$^{-3}$ mole benzhydrylamine/g. polymer, prepared by a Leuckart reductive amination of benzoylated styrene - 2% divinylbenzene copolymer gel (200 - 400 mesh) according to the method of V. J. Hruby et al (*Journal of Medicinal Chemistry*, 1973, 16, 524) ] in methylene chloride (50 ml.), the mixture cooled to 0° and treated with solid sodium carbonate (0.2g., 1.89 × 10$^{-3}$ mole). A solution of nitrosyl chloride (0.9g., 1.37 × 10$^{-2}$ mole) in methylene chloride (50 ml.) at 0° was added dropwise over 10 minutes to the stirred suspension. Faint effervescence occurred and after addition the mixture was allowed to rise to room temperature and stirred for 45 minutes when all the nitrosyl chloride had been consumed. The mixture was filtered and the polymer was washed successively with methylene chloride (50 ml.) methanol (25 ml.), water (3 × 30 ml.), methanol (25 ml.) and methylene chloride (2 × 25 ml.); and dried in vacuo at 30+ overnight. The pale yellow product (5.4g.) had ν max (Nujol) 3380 (—NH—CO), 1800 (β-lactam), 1750 (ester carbonyl), 1665 and 1497 cm$^{-1}$ (amide carbonyl).

EXAMPLE 4

Polymer Ester of (1S, 3S, 5R, 6R)-2,2-Dimethyl-6-Phenylacetamidopenam 3-Carboxylic Acid 1-Oxide via 'in situ' Oxidation of the Hydrazone of Benzoylated Styrene - 2% Divinylbenzene Copolymer Resin A stirred slurry of the hydrazone of benzoylated - 2% divinylbenzene copolymer gel (5.0g., containing 1.86 m.mole/g. of nitrogen), prepared as described above in the preparation of starting materials in methylene chloride (50 ml.), a solution of penicillin G sulphoxide acetone solvate (4.0 g, 0.98 × 10$^{-2}$ mole) in chloroform (50 ml., containing 2% v/v ethanol), and a 1% solution of iodine in methylene chloride (1.0 ml., 2.54 × 10$^{-5}$ mole) at 10° in a closed apparatus was treated with peracetic acid (1.7 ml., 0.98 × 10$^{-2}$ mole, 38% w/w in glacial acetic acid) dropwise over 10 minutes. The reaction mixture was stirred at 10° for a total of 1 hour when nitrogen (100 ml.) had been evolved. The buff reaction mixture was filtered and the polymer was washed with chloroform (4 × 50 ml.) and dried in vacuo at 40° overnight. The title polymer ester (7.4g, 96.0% attachment by esterification) was pale yellow in colour and the IR spectrum exhibited absorptions at 3380 (—NH—CO—), 1800 (β-lactam), 1750(ester carbonyl), 1665 and 1497 cm$^{-1}$ (amide carbonyl).

EXAMPLE 5 a. Polymer Diazomethylenes from Styrene - 2% Divinylbenzene Copolymer having increasing levels of Substitution in the Copolymer In a manner similar to that described above, benzolations on Styrene - 2% divinylbenzene copolymer gel (20.0g; 200 - 400 mesh, Dow Chemical Co.) using increasing amounts of benzoyl chloride and aluminium chloride gave benzolated styrene - 2% divinylbenzene copolymer resins (see Table 1). All the products exhibited the characteristic carbonyl absorption at 1661 cm$^{-1}$ in the IR spectrum. Each benzoylated polymer was converted to the corresponding hydrazone in a manner similar to that described above in the preparation of starting materials, the polymer hydrozone having satisfactory IR absorptions. The polymer hydrazones were oxidised and the resultant polymer diazomethylenes assessed for nitrogen content. All the polymer diazomethylenes exhibited the diazomethylene absorption at 2038 cm$^{-1}$ in the IR spectrum. The nitrogen content obtained for each polymer diazomethylene product is shown in Table 1. The composition for each ketone, hydazone and diazomethylene polymer was confirmed by microanalysis.

TABLE 1

Levels of Substitution and nitrogen content of polymer Diazomethylenes from Styrene - 2% Divinylbenzene Copolymer Resin

| Amount of Benzoyl Chloride Moles | Amount of Aluminium Chloride Moles | % Substitution Achieved at Benzoylation | Nitrogen Content of formed Diazoalkanes M.Mole/g. |
|---|---|---|---|
| 0.030 | 0.030 | 14.65 | 1.232 |
| 0.046 | 0.045 | 22.70 | 1.503 |
| 0.051 | 0.053 | 24.30 | 1.892 |
| 0.061 | 0.060 | 26.80 | 2.000 |
| 0.066 | 0.064 | 32.70 | 2.100 |
| 0.072 | 0.073 | 35.74 | 2.286 |
| 0.086 | 0.086 | 40.40 | 2.366 |
| 0.095 | 0.095 | 45.90 | 2.770 |
| 0.103 | 0.105 | 49.00 | 2.850 |
| 0.116 | 0.116 | 52.50 | 3.572 |
| 0.210 | 0.203 | 99.00 | 4.581 | b. Polymer Esters of (1S, 3S, 5R, 6R)-2,2-Dimethyl-6-Phenylacetamidopenam-3-Carboxylic Acid 1-Oxide via Reaction with Diazoalkanes from the Hydrazones of Benzoylated Styrene 2% Divinylbenzene Copolymer Samples of diazomethylenes from the hydrazones of benzoylated styrene - 2% divinylbenzene copolymer gel (5.0g., 200 - 400 mesh, prepared as in example 5(a) having increasing levels of substitution of the aromatic rings in the polymer) (see Table 2) as slurries in chloroform (50 ml., containing 2% v/v ethanol) were treated dropwise over 10 minutes with a solution of penicillin G sulphoxide acetone solvate (8.0 g., 1.96 × 10$^{-2}$ mole) in chloroform (50 ml., containing 2% v/v ethanol) at room temperature in a closed apparatus. Nitrogen evolved was collected by downward displacement of water. After reaction was complete (15 - 20 minutes) the mixture was filtered and the polymer was washed with chloroform (3 × 30 ml.); and dried in vacuo at 38°. In each case the polymer ester product was pale yellow in colour and the IR spectrum gave the typical absorptions aforementioned in example 3.

TABLE 2

Esterification of Penicillin G Sulphoxide Acetone Solvate with 5.0g of Polymer Diazomethylene Samples.

| % Substitution of Polymer Diazomethylene Arising from Benzoylated Polymer | Esterification | | |
|---|---|---|---|
| | Nitrogen Content as a Result of N$_2$ evoln. m. mole/g | Reaction Time Minutes | Wt. of Penicillin G Sulphoxide Polymer Ester g. |
| 14.65 | 1.282 | 15 | 6.60 |

Table 2-continued

Esterification of Penicillin G Sulphoxide Acetone Solvate with 5.0g of Polymer Diazomethylene Samples.

| % Substitution of Polymer Diazomethylene Arising from Benzoylated Polymer | Esterification | | |
|---|---|---|---|
| | Nitrogen Content as a Result of $N_2$ evoln. m. mole/g | Reaction Time Minutes | Wt. of Penicillin G Sulphoxide Polymer Ester g. |
| 22.70 | 1.503 | 25 | 7.08 |
| 24.30 | 1.892 | 30 | 7.34 |
| 26.80 | 2.000 | 30 | 7.60 |
| 32.70 | 2.180 | 45 | 7.76 |
| 35.74 | 2.286 | 50 | 7.92 |
| 40.40 | 2.366 | 60 | 8.68 |
| 45.90 | 2.770 | 60 | 9.02 |
| 49.00 | 2.850 | 60 | 9.90 |
| 52.50 | 3.572 | 105 | 10.73 |
| 99.00 | 4.581 | 120 | 13.10 |

EXAMPLE 6 a. Polymer Diazomethylenes from Styrene - 2% Divinylbenzene Copolymer Using Varying Acid Chlorides to Initially Substitute the Copolymer In a similar manner to that described above, ketone polymers of styrene - 2% divinylbenzene copolymer gel (200 - 400 mesh, Dow Chemical Co.) using varying acid chlorides were prepared (see Table 2): The carbonyl absorption in the IR spectrum for each ketone polymer is shown. Each ketone polymer was converted to the corresponding hydrazone in a similar manner to that described above in the preparation of starting materials, the polymer hydrazones having satisfactory IR absorptions. The polymer hydrazones were oxidised and the resultant polymer diazomethylenes assessed for nitrogen content. The diazomethylene absorption in the IR spectrum and the nitrogen content for each polymer diazomethylene is shown also in Table 3. The composition of each ketone, hydrazone and diazomethylene polymer was confirmed by microanalysis.

b. Polymer Esters of (1S, 3S, 5R, 6R)-2,2-Dimethyl-6-Phenylacetamidopenam-3-Carboxylic Acid 1-Oxide via Reaction with Diazoalkanes from the Hydrazones of Various Acylated Styrene - 2% Divinylbenzene Copolymers Samples of diazoalkanes from the hydrazones of various acylated styrene - 2% divinylbenzene copolymer gels (5.0g. 200 - 400 mesh, prepared as in example 6(a) (see Table 4), as slurries in chloroform (50 ml., containing 2% v/v ethanol) were treated dropwise over 10 minutes with a solution of penicillin G sulphoxide acetone solvate (8.0 g., $1.96 \times 10^{-2}$ mole) in chloroform (50 m., containing 2% v/v ethanol) at room temperature in a closed apparatus. Nitrogen evolved was collected by downward displacement of water. After reaction was complete the mixture was filtered, the polymer washed with chloroform (3 × 30 ml.) and dried in vacuo at 38°. In each case the polymer ester product was pale yellow in colour. The absorptions in the IR spectrum of each product together with the weight of polymer bound penicillin obtained are recorded in Table 4.

TABLE 3

Polymer Diazomethylenes produced from the substitution of styrene - 2% Divinylbenzene Copolymer with Varying Acid Chlorides Table 3

Polymer Diazomethylenes produced from the substitution of Styrene - 2% Divinylbenzene Copolymer with Varying Acid Chlorides

| Acid Chloride | % Substitution Achieved at Ketone formation | IR absorption cm$^{-1}$ | | Nitrogen Content of Polymer Diazoalkanes m.moles/g. |
|---|---|---|---|---|
| | | C=O of ketone | C=$N_2$ of diazalkane | |
| Acetyl | 17.6 | 1679 | 2025 | 0.714 |
| o-methoxybenzoyl | 16.3 | 1661 | 2042 | 0.116 |
| m-methoxybenzoyl | 32.2 | 1651 | 2039 | 0.740 |
| p-methoxybenzoyl | 27.0 | 1649 | 2036 | 0.067 |
| o-methoxybenzoyl | 24.0 | 1655 | 2040 | 0.669 |
| m-methylbenzoyl | 26.0 | 1655 | 2040 | 0.866 |
| p-methylbenzoyl | 23.5 | 1655 | 2038 | 1.000 |
| o-ethoxybenzoyl | 9.5 | 1659 | 2043 | 0.067 |
| m-ethoxybenzoyl | 27.5 | 1656 | 2041 | 0.330 |
| p-ethoxybenzoyl | 12.5 | 1653 | 2037 | 0.166 |
| 3,4-dimethoxybenzoyl | 15.0 | 1648 | 2037 | 0.101 |

Table 4

Esterification of Penicillin G Sulphoxide Acetone Solvate with 5.0g of Polymer Diazoalkane Samples.

| Substituent on Aromatic Rings $RC(N_2)$— R = | % Substitution of Polymer | Nitrogen evolved ex Diazoalkane in m.mole/g. polymer | Wt. of Polymer Ester Obtained g. | IR Absorptions on Polymer Esters cm$^{-1}$ | | | | |
|---|---|---|---|---|---|---|---|---|
| | | | | —NH-CO— | β Lactam | Ester Carbonyl | Amide Carbonyl | Amide Carbonyl |
| Methyl | 17.6 | 0.714 | 6.05 | 3375 | 1800 | 1735 | 1661 | 1599 |
| o-methoxyphenyl | 16.3 | 0.116 | 5.26 | 3360 | 1795 | 1739 | 1659 | 1597 |

Table 4-continued

Esterification of Penicillin G Sulphoxide Acetone Solvate with 5.0g of Polymer Diazoalkane Samples.

| Substituent on Aromatic Rings RC(N$_2$)— R= | % Substitution of Polymer | Nitrogen evolved ex Diazoalkane in m.mole/g. polymer | Wt. of Polymer Ester Obtained g. | IR Absorptions on Polymer Esters cm$^{-1}$ | | | |
|---|---|---|---|---|---|---|---|
| | | | | —NH-CO— | β Lactam | Ester Carbonyl | Amide Carbonyl / Amide Carbonyl |
| m-methoxyphenyl | 32.2 | 0.740 | 6.46 | 3380 | 1791 | 1741 | 1673   1593 |
| p-methoxyphenyl | 27.0 | 0.067 | 5.18 | 3355 | 1789 | 1729 | 1640   1581 |
| o-methylphenyl | 24.0 | 0.669 | 6.32 | 3370 | 1795 | 1748 | 1659   1600 |
| m-methylphenyl | 26.0 | 0.866 | 6.96 | 3370 | 1795 | 1746 | 1670   1600 |
| p-methylphenyl | 23.5 | 1.000 | 7.08 | 3370 | 1795 | 1747 | 1670   1598 |
| o-ethoxyphenyl | 9.5 | 0.067 | 5.08 | 3340 | 1796 | 1737 | 1663   1580 |
| m-ethoxyphenyl | 27.5 | 0.330 | 5.59 | 3370 | 1797 | 1747 | 1678   1581 |
| p-ethoxyphenyl | 12.5 | 0.166 | 5.36 | 3380 | 1799 | 1746 | 1680   1583 |
| 3,4-dimethoxyphenyl | 15.0 | 0.101 | 5.32 | 3360 | 1798 | 1741 | 1672   1578 |

EXAMPLE 7

Polymer Ester of (3S, 5R, 6R)-2,2-Dimethyl-6-Phenoxyacetamidopenam-3-Carboxylic Acid Styrene - 2% Divinylbenzene Copolymer A stirred slurry of a styrene -2% divinylbenzene copolymer based diazomethylene prepared as described in Example 5(a) (25.0 g containing 0.0513 moles diphenyldiazomethane by nitrogen assessment) in chloroform (300 ml., containing 2% v/v ethanol) at room temperature was treated portionwise over 15 minutes with penicillin V acid (30.0g, 0.085 mole). Effervescence caused by nitrogen evolution occurred, accompanied by decolourisation of the magenta polymer diazomethylene. After the addition was complete the mixture was stirred for 1 hour when the magenta colour had faded completely to a pale yellow colour. The product was filtered, washed with chloroform (2 × 200 ml., slurry wash, 2 × 200 ml., displacement wash), and dried in vacuo at 35° for 40 hours. The pale yellow title product (39.10g, containing 0.048 moles penicillin V ester, 93.5%) exhibited absorptions in the IR spectrum at ν max (Nujol): 3380 (—NHCO—), 1786 (β-lactam), 1735 (ester carbonyl), 1688 and 1597 (amide carbonyl).

EXAMPLE 8

Polymer Ester of (6R, 7R)-3-Methyl-7-Phenylacetamidoceph-3-em-4-Carboxylic Acid In a similar manner to example 7, the title polymer ester was prepared by the esterification of (6R, 7R)-3-Methyl-7-phenylacetamidoceph-3-em-4-carboxylic acid (5.0g, 1.51 × 10$^{-2}$ mole) with polymer diazoalkane (10.0g containing 1.35 × 10$^{-2}$ mole diphenyl diazomethane) prepared as described above in the preparation of starting materials in chloroform (125 ml., containing 2% v/v ethanol). The product (14.17g containing 1.35 × 10$^{-2}$ mole of the cephalosporin acid, 100%) was pale yellow in colour. ν max (Nujol): 3295 (—NH—CO—), 1775 (ν-lactam), 1720 (ester carbonyl), 1656 and 1484 cm$^{-1}$ (amide carbonyl). τ(Trifluoroacetic acid: CDCl$_3$, 1:2) 0.98 (doublet, J 8.5 Hz: —NH—) 2.72 (singlet; phenyl); 4.43 (double doublet, J4.5 Hz; 7-H), 5.0 (doublet, J 4.5 Hz; 6-H), 6.40, 6.76 (2 doublets, J 18.5 Hz; —S—CH$_2$—); 6.47 (singlet; Ph—CH$_2$—), 8.00 (singlet; —CH$_3$)

EXAMPLE 9

Polymer Ester of (1S, 6R, 7R)-3-Methyl-7-Phenylacetamidoceph-3-em-4-Carboxylic acid 1-Oxide In a similar manner to example 7, the title polymer ester was prepared by the esterification of (1S, 6R, 7R)-3-methyl-7-phenylacetamidoceph-3-em-4-carboxylic acid 1-oxide (4.0g, 0.0115 mole) with polymer diazomethylene (6.0g, 0.01 mole), prepared as described above in the preparation of starting materials in methylene chloride (150 ml.). The product (9.36g, containing 0.0103 mole/g. of cephalosporin moiety) was pale yellow in colour. ν max (Nujol) 3370 (—NHCO—), 1785 (β-lactam), 1723 (ester carbonyl), 1670 (amide carbonyl) and 1035 (sulphoxide) cm$^{-1}$ τ(trifluoroacetic acid: CDCl$_3$, 1:2) 2.45 (singlet; —NH—), 2.69 (singlet; phenyl); 3.93 (1proton double doublet, J 4.5, 9.0 Hz: 7-H) 5.18 (doublet, J 4.5 Hz; 6-H); 6.04, 6.54 (2 doublets, J 19-20 Hz; —S—CH$_2$—); 6.25 (singlet; Ph—CH$_2$—); and 7.77 (singlet; —CH$_3$). The composition of the product was confirmed by microanalysis.

EXAMPLE 10

Polymer Ester of Hydrogen Toluene-4-Sulphonate (3S, 5R, 6R)-6-Amino-2,2-Dimethyl-penam-3-Carboxylic Acid A stirred suspension of (3S, 5R, 6R)-6-amino-2,2-dimethyl-penam-3-carboxylic acid (5.4g, 0.025 mole) in acetone (20 ml.) was treated with a solution of hydrogen toluene-4-sulphonic acid (4.70g, 0.025 mole) in acetone (20 ml.) at room temperature. After stirring for 10 minutes the resultant clear solution was added in one portion to a slurry of polymer diazomethylene. (20.0g, containing 0.025 mole diphenyldiazomethane), prepared as described above in the preparation of the starting materials in methylene chloride (50 ml.). The mixture was stirred at room temperature for 1 hour, when all magenta colour had been discharged, and then filtered. The polymer was washed with methylene chloride (2 × 30 ml.), acetone (3 × 30 ml.) water (3 × 50 ml.) and methylene chloride (2 × 50 ml.); and dried in vacuo at 38° overnight. The title polymer (28.3g) was pale yellow in colour. ν max (Nujol; 2650 (NH$_3$+), 1790 (β-lactam), 1750 cm$^{-1}$ (ester carbonyl).

EXAMPLE 11

Polymer Ester of (6R, 7R)-3-Hydroxymethyl-7-(R-5-Trichlore ethyloxy-carbonylamino-5-carboxypentanamido)-ceph-3-em-4-Carboxylic Acid A stirred solution of (6R, 7R)-7-(R-5-amino-5-carboxypentanamido)-3-hydroxymethyl-ceph-3-em-4-carboxylic acid (61% 12.20g, 0.020 mole) in water (200 ml.) was adjusted to pH 8.0 with 10% w/v aqueous sodium hydroxide. Trichloroethylchloroformate (6ml., 9.42g, 0.044 mole) was added dropwise over a period of 20 minutes, with the simultaneous addition of 10% w/v aqueous sodium hydroxide to maintain the pH at 8.0. The temperature rose from 20° to a maximum of 24°. When the addition was completed, stirring was continued for 1 hour at room temperature, maintaining the pH at 8.0 with the addition of 10% w/v aqueous sodium hydroxide. Methylene chloride (100 ml.) was added, the mixture acidified to pH 5.5 with 10% w/v aqueous sulphuric acid, and the reaction mixture stirred for 15 minutes and separated. The aqueous layer was layered with ethyl acetate (100 ml.) and the pH adjusted to 2.5 with 10% v/v aqueous sulphuric acid. The ethyl acetate layer was separated, and the aqueous layer extracted with ethylacetate (2 × 100 ml.). The combined ethylacetate extracts were washed with 0.5M sodium chloride solution (100 ml.) and water (2 × 100 ml.) dried (anhydrous sodium sulphate), and concentrated to approximately 100 ml. under reduced pressure at room temperature. The ethylacetate extract was added, in one portion, to a stirred suspension of polymer diazomethylene (11.50g, 0.0166 mole), prepared as described above in the preparation of starting materials in methylene chloride (100 ml.) at room temperature. The reaction mixture was stirred for 48 hours at room temperature. Effervescence caused by nitrogen evolution was accompanied by decolourisation of the magenta diphenyldiazomethane polymer. The reaction mixture was filtered and pulled as dry as possible. The product was washed with methanol (3 × 100 ml.), water (4 × 100 ml.), methanol (2 × 100 ml.) and methylene chloride (3 × 100 ml.). The product was dried to constant weight in vacuo at 25° to a golden yellow bis polymer ester of (6R, 7R)-3-hydroxymethyl-7-(R-5-trichloroethyloxycarbonylamino-5-carbpxypentanamido)-ceph-3-em-4-carboxylic acid (18.62g). From the gain in weight, the cephalosporin moiety corresponds to 0.000696 mole/g. of polymer. $\nu$ max (Nujol): 3315m (NH) 1795s ($\beta$-lactam CO), 1730s (ester CO), and 1665s (amide CO), $\tau$ (Trifluoroacetic acid: CDCl$_3$, 1:2) 3.24 (doublet; J 8 Hz; 7-NH), 4.09 (double (doublet doublet; J 4.5 and 9.0 Hz; 7-H), 4.82 (doublet; J 5 Hz; 6H), 6.08, 6.47 (two doublets; J 18 Hz; —S—CH$_2$—), 7.49 (triplet; J 6 Hz; —CH$_2$—CH$_2$—CONH—), and 8.04 (multiplet, >CH—CH$_2$—CH$_2$—CH$_2$CONH).

EXAMPLE 12

Polymer Ester of (1S, 3S 5R, 6R)-2,2-Dimethyl-6-Phenoxyacetamidopenam-3-Carboxylic Acid 1-Oxide by Oxidation of the Corresponding Sulphide A stirred slurry of the styrene- 2% divinylbenzene copolymer ester of (3S, 5R, 6R)-2,2-dimethyl-6-phenoxyacetamidopenam-3-carboxylic acid (20.0g), from example 7, in methylene chloride (200 ml.) at 0° was treated with peracetic acid (5.0 ml., 2.84 × 10$^{-2}$ mole) dropwise over 10 minutes. After the addition the mixture was allowed to attain room temperature and was then stirred for a further 30 minutes and then filtered. The polymer was washed with methylene chloride (2 × 50 ml.) and dried in vacuo at 38° overnight. The title polymer (20.4g) was pale yellow in colour and exibited $\nu$ max (Nujol) 3355 (—NH—CO—), 1788 ($\beta$-lactam), 1736 (ester carbonyl), 1683 and 1595 (amide carbonyl), 1017 cm$^{-1}$ (sulphoxide). A portion of the polymer product (0.20g) was shaken at room temperature for 10 seconds with a mixture of chloroform/trifluoroacetic acid (1 ml., 2:1) and t.l.c. of this solution on silica gel. eluting with a mixture of butyl acetate; butan-1-ol:methanol: glacial acetic acid: water; 80:15:5:4::24; and visualising with tetrazolium blue, indicated 100% conversion of the sulphide to the corresponding sulphoxide.

EXAMPLE 13

Polymer Ester of (1S, 6R, 7R)-3-Methyl-7-Phenylacetamidoceph-3-em-4-Carboxylic Acid 1-Oxide by Oxidation of the Corresponding Sulphide To a stirred suspension of polymer ester of (6R, 7R)-3-methyl-7-phenylacetamidoceph-3-em-4-carboxylic acid (5.00g, 4.45 mole, from example 8 in methylene chloride (35 ml.) and methanol (10 ml.) cooled to 0° was added peracetic acid (38% w/v, 1.1 ml., 5.50 m.mole) in one portion. Stirring was continued for 30 minutes at 0° and for a further 15 minutes, after removal of the cooling bath. The reaction mixture was filtered and pulled as dry as possible. The product was washed with methylene chloride (2 × 50 ml.) methanol (2 × 50 ml.), and methylene chloride (2 × 50 ml.). The product was dried to constant weight in vacuo at 30° to give the pale yellow polymer ester of (1S, 6R. 7R)-3-methyl-7-phenylacetamidoceph-3-em-4-carboxylic acid 1-oxide (5.00g, which proved to be similar (infra red, nmr., and t.l.c.) with the product obtained in example 9 above.

EXAMPLE 14

Polymer Ester of (3S, 5R, 6R)-2,2-Dimethyl-6-Phenoxyacetamidopenam-3-Carboxylic Acid by Sulphoxide Reduction A stirred slurry of the styrene - 2% divinylbenzene copolymer ester of (1S, 3S, 5R, 6R)-2,2-dimethyl-6-phenoxyacetamidopenam-3-carboxylic acid 1-oxide (3.0g), from example 12, in dioxan (50 ml.) at room temperature was treated with potassium iodide (3.0g, 1.81 × 10$^{-2}$ mole). The slurry was stirred at room temperature for 90 minutes during which time iodine was slowly liberated as the reduction proceeded. The mixture was then filtered and the polymer washed with dioxan (2 × 50 ml.), methylene chloride (30 ml.), dioxan (30 ml.), water (2 × 100 ml.), 1% sodium thiosulphate solution (2 × 50 ml.), water (100 ml.), dioxan (30 ml.) and methylene chloride (2 × 50 ml.): and dried in vacuo at 40° overnight. The product (2.95g) was pale yellow in colour and the IR spectrum was identical in all respects with that from example 7 above (absence of sulphoxide absorption at 1017 cm$^{-1}$). A portion of the polymer product (0.2g) was shaken at room temperature for 10 seconds with a mixture of chloroform/trifluoroacetic acid (1 ml., 2:1) and t.l.c. of this solution on silica gel eluting with a mixture of butylacetate: butan-1-ol:methanol:glacial acetic acid:water: 80:15:5:4:24: and location by tetrazolium blue indicate greater than 90% of the penicillin sulphide present and only 5 – 10% of unreduced penicillin sulphoxide.

EXAMPLE 15

Reduction of Polymer Ester of (1S, 6R 7R)-3-Methyl-7-Phenylacetamido-ceph-3-em-4-Carboxylic Acid 1-Oxide To a stirred suspension of polymer ester of (1S, 6R, 7R)-3-methyl-7-phenylacetamidoceph-3-em-4-carboxylic acid 1-oxide (2.00g, 2.06 m.mole, from example 9 in acetonitrile (25 ml.) and methylene chloride (15 ml.) was added sodium dithionite (1.08g, 6.21 m.mole) and acetyl chloride (1 ml., 1.10g, 0.014 mole). The reaction mixture was stirred for 24 hours at room temperature (18° – 21°) when the initial pale yellow suspension turned deep brown in colour. The reaction mixture was filtered and pulled as dry as possible. The product was washed with methylene chloride (3 × 40 ml.), methanol (2 × 40 ml.), water (4 × 40 ml.) and methylene chloride (3 × 40 ml.). The product was dried to constant weight in vacuo at 30° to give the dark brown polymer ester of (6R, 7R)-3-methyl-7-phenylcetamidoceph-3-em-4-carboxylic acid (1.85g). Infra red, nmr, and t.l.c. were consistent with the product obtained in example 8 above, and indicated that reduction had proceeded to approximately 90% completion.

EXAMPLE 16

Polymer Ester of (6R, 7R)-3-Methyl-7-Phenylacetamidoceph-3-em-4-Carboxylic Acid (by Thermal Ring Expansion)

The polymer ester of (1S, 3S, 5R, 6R)-2,2-dimethyl-6-phenylacetamido-penam-3-carboxylic acid 1-oxide (195.85g, containing 0.173 mole penicillin moiety [prepared as in example 5(b) from the polymer diazomethylene of the hydrazone of benzoylated styrene - 2% divinylbenzene copolymer (127.3g, 27% substituted) and penicillin G sulphoxide acetone solvate (70.4g, 0.174 mole)] and mono (2,2,2-trichloroethyl) phosphate (4.3g) were heated under reflux with stirring in dioxan (1.0 l) containing dry pyridine (1.6 ml.) for 24 hours, the reflux return being passed continuously through sodium hydroxide pellets during this period. The mixture was cooled to room temperature and filtered and the polymer was washed with dioxan (2 × 250 ml.) and methylene chloride (3 × 250 ml.); then dried in vacuo at 38° to constant weight. The product resin (186.8g) was dark brown in colour and was identical in all respects (IR, NMR) with the product of example 8.

EXAMPLE 17 p-Methoxy-substituted Polymer Ester of (6R, 7R)-3-Methyl-7-Phenylacetamido-ceph-3-em-4-Carboxylic Acid (by Thermal Ring Expansion)

In a similar manner to that of example 16 the polymer ester of (1S, 3S, 5R, 6R)-2,2-dimethyl-6-phenylacetamidopenam-3-carboxylic acid 1-oxide (30.0g, containing 1.91 × 10$^{-2}$ mole of penicillin moiety) [prepared as in example 6(b) from the polymer diazoalkane of the hydrazone of p-methoxybenzoylated styrene - 2% divinylbenzene copolymer (24.5g, prepared as in example 6(a)] and penicillin G sulphoxide acid acetone solvate (7.0g); was converted to the title polymer. The product (28.40g) was brown in colour and the IR and NMR spectrum were consistent with those of the title compound.

EXAMPLE 18

Polymer Ester of (6R,7R)-7-Amino-3-Methylceph-3-em-4-Carboxylic Acid

Dry pyridine (48.0 ml., 0.595 mole) in methylene chloride (200 ml.) was added dropwise over 10 minutes to a stirred suspension of phosphorus pentachloride (126.0g, 0.600 mole) in methylene chloride (1.0 l) and the mixture stirred at 25° – 30° for 20 minutes and then cooled to −15°. The polymer ester of example 16 (186.7g, 0.173 mole) was then added and washed in with methylene chloride (200 ml). The brown slurry was stirred at 14° – 18° for 2 hours, cooled to −10° and treated with a cold mixture of butane-1:3-diol (166g, 1.84 moles) in methylene chloride (300 ml) over 5 minutes such that the temperature did not rise above −5°. The mixture was then stirred between 0° and 5° for 20 minutes and treated with water (400 ml) and stirred at 5° for a further 20 minutes. The mixture was filtered and the polymer washed with methylene chloride (2 × 250 ml), methanol (250 ml), water (2 × 200 ml), methanol (400 ml) and methylene chloride (2 × 250 ml.); and dried in vacuo at 38° to constant weight. The ginger title polymer (168.8g) exhibited $\nu$ max (Nujol) 3170 (—NH$_2$), 1795 ($\beta$-lactam), 1720 (ester carbonyl). $\tau$ (CDCl$_3$:trifluoroacetic acid; 2:1) 4.71 (doublet, J 4.5 Hz; 7-H); 4.84 (doublet J 4.5 Hz; 6-H): 6.35, 6.76 (2 doublets, J 16.5 Hz; —S—CH$_2$—): 7.61 (singlet; —CH$_3$).

EXAMPLE 19

Polymer Ester of (3S, 5R, 6R)-6-Amino-2,2-Dimethylpenam-3-Carboxylic Acid

Pyridine (4.5 ml, 4.74g, 0.06 mole: dried over KOH) was added over 10 minutes to a stirred suspension of phosphorus pentachloride (6.24g, 0.03 mole) in dry methylene chloride (100 ml.) under nitrogen at room temperature (18° – 21°), and when the addition was completed the reaction mixture was stirred for 30 minutes at room temperature (18° – 21°). The reaction mixture was cooled to −15° and the polymer ester of (3S,5R,6R)-2,2-dimethyl-6-phenoxyacetamidopenan-3-carboxylic acid (17.00g, 0.02 mole; from example 5) was added. The addition was accompanied by a rise in temperature of 4°. The mixture was stirred for 3 hrs. at −15°, then cooled to −50° and methanol (100 ml.) added, keeping the temperature at −50° to −45°. When the addition of methanol was completed, the resulting brown mixture was stirred for 2 hours allowing the temperature to rise to −15°. Water (100 ml) was added at 0° and the resulting yellow mixture stirred for 1 hour allowing the temperature to rise to room temperature (18° – 21°). The reaction mixture was filtered and pulled as dry as possible. The product was washed with methylene chloride (3 × 100 ml), methanol (2 × 100 ml), water (3 × 100 ml), methanol (2 × 100 ml) and methylene chloride (3 × 100 ml). The product was dried to constant weight in vacuo at room temperature (18° – 21°) to give a yellow coloured polymer ester of (3S, 5R, 6R)-6-amino-2,2-dimethylpenam-3-carboxylic acid (16.10g). A sample of the product on suspending in methylene chloride, spraying with a 0.5% solution of ninhydrin in butan-1-ol and warming gave a deep-red purple colouration. The polymer ester of (3S,5R,6R)-2,2-dimethyl-6-phenoxyacetamidopenam-3-carboxylic acid gave, under the same conditions, a negative test with ninhydrin. ν max (Nujol) 1787s (β-lactam CO), and 1738s (ester CO).

EXAMPLE 20

(6R, 7R)-7-Amino-3-Methylceph-3-em-4-Carboxylic Acid

The polymer product of example 18 above (26.6g) in methylene chloride (125 ml) and trifluoroacetic acid (125 ml) was stirred at room temperature for 25 minutes. The residual polymer was removed by filtration, washed with methylene chloride (3 × 50 ml) and dried in vacuo at 38° overnight to give a ginger solid (22.0g). The filtrate and washings, from above, were rapidly evaporated under reduced pressure and the residual brown oil was triturated with a mixture of diethyl ether and petroleum ether (100 ml., 1:1). The brown slurry was then stood at 0° for 1 hour, filtered and the solid was washed with cold diethyl ether (10 ml). The crude (6R,7R)-7-amino-3-methylceph-3-em-4-carboxylic acid was slurried in water (100 ml) and treated with 50% aqueous ammonia (ca. 5 ml) to pH 8.0 and the mixture stirred to solution: charcoal (10.0g) was added and the mixture further stirred for 15 minutes and filtered. The cake was washed with water (2 × 25 ml) and the combined filtrate and washings were lowered to pH 5.5 with concentrated hydrochloric acid (2 ml). The buff solution was treated with a seed of (6R, 7R)-7-amino-3-methylceph-3-em-4-carboxylic acid (0.01g) and stirred for 5 minutes. The pH of the mixture was then lowered to 3.8 with concentrated hydrochloric acid, the slurry cooled to 0° and stirred for 1 hour. The solid was filtered, washed with water (2 × 50 ml): and dried in vacuo at 38° overnight to give the title compound (3.45g, 63.05% yield overall from penicillin G sulphoxide acetone solvate, used in examples 16 and 18). Thin layer chromatography of the product on silica gel eluting with butyl acetate, water, acetic acid, butan-1-ol, methanol, 80:40:24:15:5: and visualisation either by UV irradiation or by spraying the plate with 0.5% solution of ninhydrin in butan-1-ol followed by warming, indicated single spot material (Rf 0.04). IR and NMR spectra were identical with those of an authentic sample. $[a]_D^{20}$ 153° (c. 0.5 in 0.2M, pH 7.0 phosphate buffer).

EXAMPLE 21

(6R, 7R)-7-Amino-3-Methylceph-3-em-4-Carboxylic Acid

The polymer ester of the title compound (5.0g) prepared as in example 18 was slurried in chloroform (20 ml, containing 2% v/v ethanol) and 90% formic acid (15 ml) for 10 minutes and then the mixture was poured into a glass column and the liquor allowed to drain. When the resin bed was almost dry the polymer was eluted with a mixture of chloroform (20 ml, containing 2% v/v ethanol), 90% formic acid (15 ml) and methanesulphonic acid (0.3 ml) in three portions. The total eluate was rapidly evaporated under reduced pressure to a viscous yellow oil, which was dissolved in water (20 ml) and the stirred solution treated with 0.880 ammonia solution to pH 4.0. After cooling at 0° the solid was filtered, washed with water (2 × 15 ml) and dried in vacuo at 35° to constant weight. (6R,7R)-7-amino-3-methylceph-3-em-4-carboxylic acid (0.885g, 80.4%) was isolated as an off-white crystalline solid whose IR and NMR spectra and t.l.c. were identical with those of an authentic sample. $[a]_D^{20}$ 155° (c.0.4 in 0.2M, pH 7.0 phosphate buffer, E 360 at 263nm).

EXAMPLE 22

Sodium (6R,7R)-3-Methyl-7-Phenylacetamidoceph-3-em-4-Carboxylate

The polymer ester of (6R,7R)-3-methyl-7-phenyolacetamidoceph-3-em-4-carboxylic acid (10.0g), prepared as in example 8, was slurried at room temperature in a mixture of chloroform (15 ml containing 2% v/v ethanol) and 98% formic acid (20 ml) for 10 minutes. The mixture was transferred to a glass column and allowed to drain. The almost dry polymer was then eluted at ca. 2ml/minute with a mixture of chloroform and formic acid (150 ml, 3:4) containing toluene 4 - sulphonic acid (1.0g). The total eluate was stirred and cooled to 10° and then treated dropwise over 15 minutes with a solution of sodium hydroxide. (50.0g) in water (200 ml). After a further 30 minutes at 10° the solid was filtered, washed with chloroform (50 ml) and diethyl ether (2 × 50 ml) and dried in vacuo at 35° overnight. The title compound (2.01g, 61.5% was white in colour and the IR and NMR spectra and t.l.c. were identical with those of an authentic sample. $[a]_D^{20}$ 177° (c. 2% in methanol).

EXAMPLE 23

(6R,7R)-7-Amino-3-Methylceph-3-em-4-Carboxylic Acid

Dry pyridine (2.0 ml. 2.4 × $10^{-2}$ mole) was added dropwise over 1 minute to a stirred suspension of phosphorus pentachloride (5.12g, 2.4 × $10^{-2}$ mole) in methylene chloride (50 ml.) and the mixture stirred at 25°-30° for 25 minutes and then cooled to −10°. The polymer ester of (6R,7R)-3-methyl-7-phenylacetamidoceph-3-em-4-carboxylic acid (10.5g, containing 1.04 × $10^{-2}$ mole cephalosporin moiety) prepared as in example 8, was then added and washed in with methylene chloride (30 ml.). The slurry was stirred at room temperature for 90 minutes, cooled to −10° and treated with methanol (5.0 ml) such that the temperature did not rise above 0°. After stirring for 10 minutes further methanol (8 ml) was added and the mixture was stirred at room temperature for 30 minutes. The mixture was then filtered directly with no water treatment and the polymer was washed with methylene chloride (4 × 50 ml), and pulled dry. The damp polymer was slurried directly in 98% formic acid (25 ml) and the mixture poured into a glass column. The polymer was eluted with a mixture of methylene chloride/formic acid (140 ml, 1:1) containing toluene-4-sulphonic acid (4.2g). The combined eluate was evaporated and the residue worked-up as in example 21 to afford the title acid (0.815g, 36.8%) as an off-white crystalline solid. The IR and NMR spectra and t.l.c. of the product were identical with those of an authentic sample. $[a]_D^{20}$ 150° (c. 0.5 in 0.2M, pH 7.0 phosphate buffer).

EXAMPLE 24

Polymer Ester of(1S,3S,5R,6R)-2,2-dimethyl-6-Phenylacetamidopenam-3-Carboxylic Acid 1-Oxide via the Oxidatively Regenerated Polymer Diazoalkane from the Hydrazone of Benzoylated Styrene - 2% Divinylbenzene Copolymer The residual resin arising from the trifluoroacetic acid cleavage reaction of example 20 (10.0g) was heated under reflux with stirring in 30% aqueous nitric acid (200 ml) for 90 minutes. Considerable effervescence with the evolution of nitrogen dioxide occurred, the brown polymer lightening in colour considerably during reaction. After cooling to room temperature, the mixture was filtered and the polymer was washed with water (3 × 100 ml) and dried in vacuo at 38° overnight. The pale yellow polymer (8.75g) was then heated under reflux with stirring in 10% aqueous sodium hydroxide solution (150 ml) for 2 hours. After cooling to room temperature the mixture was filtered, the polymer washed with water (3 × 100 ml) and dried in vacuo at 40° overnight. The product (7.79g) was yellow in colour and the IR spectrum exhibited the characteristic carbonyl absorption at 1660 cm$^{-1}$ for benzoylated styrene — 2% divinylbenzene copolymer. The benzoylated polymer from above (6.5g) in butan-1-ol (50ml) was treated with 99% hydrazine hydrate (20.0 ml) and the mixture was heated under reflux with stirring for 24 hours, and then cooled to room temperature and filtered. The polymer hydrazone was washed with butan-1-ol (30 ml), methanol (2 × 25 ml) and methylene chloride (2 × 50 ml) and dried in vacuo at 40° to constant weight. The product (6.48g) was orange in colour.

The above polymer hydrazone (6.48g) in methylene chloride (75 ml) was treated with 1,1,3,3-tetramethylguanidine (10.0 ml., 7.94 × 10$^{-2}$ mole) followed by a 1% solution of iodine in methylene chloride (1.0 ml, 2.54 × 10$^{-5}$ mole) and cooled to −5°. Peracetic acid (4.2 ml, 2.39 × 10$^{-2}$ mole, 38% w/w in glacial acetic acid) was then added dropwise over 20 minutes while the reaction temperature was maintained at −5°. After addition the mixture was stirred for a further 30 minutes while allowing the temperature to rise to room temperature and then filtered. The magenta polymer was washed with methylene chloride (3 × 50 ml) and dried in vacuo at room temperature overnight. The polymer diazomethylene (6.67g) was magenta in colour, and the IR spectrum exhibited the characteristic diazoalkane absorption at 2040 cm$^{-1}$. Assessment of the above polymer diazomethylene by esterification of penicillin G sulphoxide acetone solvate in the usual way afforded nitrogen (212 ml) and the title polymer ester (6.67g) as a yellow solid which was identical in all respects with an authentic sample from example 5(b) above. The nitrogen content of the regenerated polymer diazomethylene was 1.892 m.moles/g, of polymer (78.4% of the original activity of polymer diazoalkane used in example 16.

EXAMPLE 25

Polymer Ester of (6R,7R)-3-Methyl-7-(2-Thienyl) acetamidoceph-3-em-4-Carboxylic Acid A suspension of the polymer ester of (6R,7R)-7-amino-3-methylceph-3-em-4-carboxylic acid (5.00g, 5.0 m.mole, from example 18) in methylene chloride (100 ml) was stirred at room temperature (18°–21°) under nitrogen for 30 minutes. After cooling to 0°, triethylamine (3.03g. 0.03 mole) was added, and stirring continued for 30 minutes. Thienylacetyl chloride (3.0 ml, 3.89g, 0.024 mole) was then added dropwise over a period of 10 minutes maintaining the temperature at 0°–5°. When addition was completed stirring was continued for 15 minutes at 0°–5° and for a further 5 hours at room temperature (18°–21°). The reaction mixture was filtered and pulled as dry as possible. The product was washed with methylene chloride (3 × 100 ml) acetone (2 × 100 ml), water (4 × 100 ml), acetone (2 × 100 ml), and methylene chloride 3 × 100 ml): and dried to constant weight in vacuo at 40° to give a light brown coloured polymer ester of (6R,7R)-3-methyl-7-(2-thienyl) acetamidoceph-3-em-4-carboxylic acid (5.41g). The composition was confirmed by microanalytical data. ν max (Nujol) 3320w (NH), 1780s (β-lactam CO), 1722s (ester CO) abnd 1688s (amide CO) cm$^{-1}$, τ [CDCl$_3$ and CF$_3$COOH (2:1)] 2.66 (triplet, J = 3.3 Hz: 2-thienyl proton), 2.97 (doublet, J = 3.3 Hz: 3-thienyl protons): 4.27 (double doublet, J 4.5; 9.0 Hz; 7-H), 4.88 (doublet J 4.5 Hz: 6-H), 5.99 (singlet: —CH$_2$CO—), 6.41 and 6.77 ( 2 doublets, J 18 - 19 Hz: s-CH$_2$), and 7.70 (singlet, —CH$_3$).

EXAMPLE 26

Polymer Ester of (3S, 5R, 6R)-2,2-Dimethyl-6-(2-Thienylacetamido) penam-3-Carboxylic Acid A suspension of the polymer ester of (3S, 5R, 6R)-6-amino-2,2-dimethyl penan-3-carboxylic acid (4.00g., 0.005 mole, from example 19 was stirred in methylene chloride (100 ml.) under nitrogen for 30 minutes at room temperature (18°–21°). The mixture was cooled to 0° and triethylamine (3.03g., 0.03 mole) was added, and stirring continued for 30 minutes. Thienylacetyl chloride (3.0 ml., 3.89g., 0.024 mole) was added dropwise over a period of 10 minutes maintaining the temperature 0°–5°. When the addition was completed, stirring was continued for 15 minutes at 0°–5° and then for a further 5 hours allowing the temperature to rise to room temperature (18°–21°). The reaction mixture was filtered and pulled as dry as possible. The product was washed with methylene chloride (3 × 50 ml.), acetone (2 × 50 ml.), water (4 × 50 ml.), acetone (2 × 50 ml.) and methylene chloride (3 × 50 ml.) and dried to constant weight in vacuo at room temperature (18°–21°) to give a yellow coloured polymer ester of (3S, 5R, 6R)-2,2-dimethyl-6-(2-thienylacetamido) penam-3-carboxylic acid (4.40g). A sample of the product on suspending in methylene chloride, spraying with a 0.5% solution of ninhydrin in butan-1-ol and warming gave no characteristic colouration. ν max (Nujol) 3340w (NH), 1788s (β-lactam CO), 1740s (ester CO) and 1674s (amide CO).

EXAMPLE 27

Polymer Ester of (1S, 3S, 5R, 6R)-2,2-Dimethyl-6-Phenylacetamidopenam-3-Carboxylic Acid 1-Oxide A suspension of α-hydroxybenzyl polystyrene - 2% divinylbenzene coplymer [(10.0g., 0.029 mole) prepared according to the method G. L. Southard et al; Tetrahedron 1971, 27, 2701] in methylene chloride (50 ml.) was stirred for 1 hour at room temperature (18°–21°) to swell the polymer. To the suspension cooled to 5° was added (1S, 3S, 5R,6R)-2,2-dimethyl-6-phenylacetamidopenam-3-carboxylic acid 1-oxide acetone solvate (20.40 g., 0.05 mole), followed by Toluene-p-sulphonyl chloride (14.30g., 0.075 mole), pyridine (12.1 ml., 11.85g., 0.15 mole; dried over KOH) and acetone (25 ml.). The mixture was stirred for 4 hours at 5°– 10°, during which an intense green colouration developed. The reaction mixture was filtered and pulled as dry as possible. The product was washed with chloroform (3 × 100 ml., containing 2% v/v ethanol), methanol (2 × 100 ml.), water (4 × 100 ml.), methanol (2 × 10 ml.) and chloroform (2 × 100 ml., containing 2% v/v ethanol); and drid to constant weight in vacuo at room temperature (18°–21°) to give a pale yellow polymer ester of (1S, 3S, 5R, 6R)-2,2-dimethyl-6-phenylacetamidopenam-3-carboxylic acid 1-oxide (19.97g.). The composition was confirmed by microanalytical data and the infra red spectrum was identical with the product obtained in example 6 above. From the gain in weight, the penicillin moiety corresponds to 1.43 m.mole/g. of polymer.

EXAMPLE 28

Esterification of (1S, 3S, 5R, 6R)-2,2-Dimethyl-6-Phenylacetamidopenam-3-Carboxylic Acid 1-Oxide with a Poly(styrene-allyl alcohol) Copolymer To a stirred solution of poly(styrene-allyl alcohol) copolymer(7.00g. 0.0316 mole, Polysciences Inc. Cat. No. 3774, Lot No. 251 - 6, containing 7.7% OH) in methylene chloride (50 ml.) cooled to 5° was added (1S, 3S, 5R, 6R)-2,2-dimethyl-6-phenylacetamidopenam-3-carboxylic acid 1-oxide acetone solvate (13.90g., 0.034 mole), followed by toluene-p-sulphonyl chloride (9.70g., 0.051 mole) and pyridine (8.3 ml., 8.13g., 0.103 mole; fried over KOH). The mixture was stirred for 2 hours at 5°–10°, during which time the initially colourless reaction mixture went a yellow-green colour and finally brown in colouration. The methylene chloride was washed with water (3 × 50 ml.), dried (anhydrous $Na_2SO_4$) and evaporated to dryness under reduced pressure. The residue was taken up in acetone (50 ml.) treated with charcoal for 30 minutes at room temperature (18°–21°), and after filtering, the filtrate was added, with vigorous stirring to water (200 ml.) kept at 47°. The sticky yellow precipitate that formed, solidified on cooling, and after 12 hours at 0° was ground to a powder. The product was filtered and washed well with water (20 × 100 ml.), and dried in vacuo to constant weight at 30° to give a light yellow coloured poly(styrene-allyl alcohol) copolymer derived ester of (1S, 3S, 5R, 6R)-2,2-dimethyl-6-phenylacetamidopenan-3-carboxylic acid 1-oxide. The composition was confirmed by microanalytical data. ν max (Nujol) 3360w (NH) 1798s (βlactam CO), 1750m (ester CO) and 1683m (amide CO). From the gain in weight the penicillin moity corresponds to 1.59 m.mole/g. of polymer.

EXAMPLE 29 a. Polymer Ester of (1S, 5R, 6R)-2,2-Dimethyl-6-Phenylacetamidopenam-3-Carboxylic Acid 1-Oxide Polymer diazomethylene (50.000g, 0.093 mole, prepared as described above in the preparation of starting materials) was esterified with penicillin G sulphoxide acid acetone solvate (50.000g, 0.123 mole) as in example 5(b) to give the polymer ester of (1S, 5R, 6R -2,2-dimethyl-6-phenylacetamidopenam-3-carboxylic acid 1-oxide (81.20g.). Based on weight gain the penicillin moiety corresponds to 1.09 m.mole/g. of polymer. The IR spectrum was similar with the product obtained in example 5 above.

b. Polymer Ester of (6R, 7R)-3-Methyl-7-Phenylacetamidoceph-3-em-4-Carboxylic Acid The polymer ester of (1S, 5R, 6R)-2,2-dimethyl-6-phenylacetamidopenam-3-carboxylic acid 1-oxide[45.60g, 0.05 mole, from example 29(a)] was refluxed for 24 hours in dioxan (500 ml.) with trichloroethylphosphate (1.15g, 5.0 m.mole) and pyridine (0.41 ml., 0.40g, 0.0051 mole) as in example 16 above to give the polymer ester of (6R, 7R)-3-methyl-7-phenylacetamidoceph-3-em-4-carboxylic acid (40.65g). The IR and NMR spectra were identical with the product obtained in example 8 above.

c. Polymer Ester of (6R, 7R)-7-Amino-3-Methylceph-3-em-4-Carboxylic Acid

The polymer ester of (6R, 7RO-3-methyl-7-phenylacetamidoceph-3-em-4-carboxylic acid [40.00g, from example 29(b)] was treated — with phosphorus pentachloride (20.85g, 0.10 mole) and pyridine — (8.1 ml., 7.90 g, 0.1 mole) in methylene chloride as in example 18 above to give the polymer ester of (6R, 7R)-7-amino-3-methylceph-3-em-4-carboxylic acid (38.28g). The IR and NMR spectra were identical with the product obtained in example 18 above d. Polymer Ester of (6R, 7R)-3-Methyl-7-(D-a-2',2',2'-Trichloroethyloxy-carbonylaminophenylacetamido)-ceph-3-em-4-Carboxylic Acid A suspension of polymer ester of (6R, 7R)-7-amino-3-methylceph-3-em-4-carboxylic acid [10.00g, from example 29(c)] in methylene chloride (100 ml.) was stirred for 30 minutes under nitrogen at room temperature. The suspension was cooled to 0° and triethylamine (6.06g, 0.06 mole) was added. After 30 minutes at 0°, a solution of N-(R-α-2',2',2'-trichloro ethyloxycarbonyl)phenylglycyl chloride (10.35g, 0.03 mole) in methylene chloride (50 ml.) was added dropwise over a period of 10 minutes whilst maintaining the temperature between 0° and 5°. After a further 15 minutes at 0° – 5°, the reaction mixture was allowed to warm to room temperature and stirred for 5 hours. The reaction mixture was filtered and pulled as dry as possible. The product was washed with methylene chloride (3 × 100 ml.), methanol (2 × 100 ml.), water (4 × 100 ml.), methanol (2 × 100 ml.) and methylene chloride (3 × 100 ml.) dried to constant weight in vacuo at 40° to give a brown coloured polymer ester of (6R, 7R)-3-methyl-7-(R-α-2',2',2'-trichloroethyloxy-carbonylaminophenylacetamido) ceph-3-em-4-carboxylic acid (11.21 g), T.l.c. of the product on silica gel and developed with n-butyl acetate, butan-1-ol, glacial acetic acid and water (80:15:14:15) after cleavage with trifluoroacetic acid in methylene chloride indicated the presence of the title compound (as its acid) (Rf 0.52) which proved to be identical with an authentic sample of (6R, 7R)-3-methyl-7-(R-α-2',2',2'-trichloro ethyloxycarbonylaminophenylacetamido)-ceph-3-em-4-carboxylic acid run under the same conditions. ν max (Nujol) 3340 (NH), 1775 (β-lactam CO) and 1724 (ester and carbonate CO) cm$^{-1}$, τ (tri-fluoroacetic acid: CDCl$_3$, 1:2) 2.57 (singlet; aromatic), 4.42 (centre of multiplet for C-7H and PhCH-), 4.97 (doublet, J 4 Hz; C - 6H), 5.24 (singlet; —CH$_2$CCl$_3$), 6.47, 6.82 (two doublets, J18 Hz; C-2 H$_2$), and 7.74 (singlet; C-3 CH$_3$).

e. (6R, 7R)-3-Methyl-7-(D-a-2',2',2'-trichloroethyloxycarbonylamino-phenylacetamido)ceph-3-em-4-Carboxylic Acid from the Polymer Ester of (6R, 7R)-3-Methyl-7-(D-a-2',2',2'-trichloroethyloxycarbonyl-aminophenylacetamido)ceph-3-em-4-Carboxylic acid A suspension of polymer ester of (6R, 7R)-3-methyl-7-(R-α-2',2',2'-trichloroethyloxycarbonylamino-phenylacetamide)ceph-3-em-4-carboxylic acid [5.00g, from example 29(d)] in chloroform (50 ml., containing 2% v/v ethanol) and trifluoroacetic acid (25 ml.) was stirred for 30 minutes at 35°. The dark reaction mixture was filtered, pulled as dry as possible and the polymer was washed with chloroform (4 × 50 ml., containing 2% v/v ethanol). The combined chloroform filtrates were evaporated to dryness under reduced pressure at <25°, the dark brown oily residue was taken up in a saturated solution of sodium hydrogen carbonate and washed with ethyl acetate (2 × 50 ml). The aqueous solution was collected, and after treatment with charcoal (1.00 g) for 30 minutes at room temperature, the filtrate was layered with ethyl acetate (75 ml.) and the pH adjusted to 2.0 with concentrated hydrochloric acid. The ethyl acetate layer was collected and combined with further ethyl acetate extracts (2 × 75 ml.) of the aqueous layer. The combined ethyl acetate solution was washed with water (100 ml.) and a saturated solution of sodium chloride (100 ml.) dried (anhydrous sodium sulphate) and evaporated to give a brown oil. The residue was cooled to <10° and triturated with diethyl ether (25 ml.) and the precipitate filtered, washed with a small volume of ice-cold diethyl ether and dried to constant weight in vacuo at room temperature to give (6R, 7R)-3-methyl-7-(D-a-2',2',2'-trichloroethyloxycarbonylamino-phenylacetamido)ceph-3-em-4-carboxylic acid (75.5 mg). From the filtrate a second crop of (6R, 7R)-3-methyl-7-(R-α-2',2',2-trichloro-ethylcarbonylaminophenylacetamido)ceph-3-em-4-carboxylic acid was isolated (65.5 mg). IR and t.l.c. of the product on silica gel and developed with n-butyl acetate, butan-1-ol, glacial acetic acid and water (80:15:14:15) indicated the presence of the titled compound which proved to be identical with an authentic sample. $\nu$ max 3670 – 2500 m$^b$ (OH), 3280m (NH), 1763s ($\beta$-lactam CO), 1718s (ester and carbonate CO) and 1663s (amide CO) cm$^{-1}$. $\tau$ [(CD$_3$)$_2$SO] 0.85 (doublet, J 8 – 9 Hz; C-7 -CONH-), 1.61 (doublet, J 9 Hz; -OCONH-). 2.2 – 2.9 (multiplet, aromatic and —COOH) 4.52 (double doublet, J 4.5 and 8 – 9 Hz; C-7H), 4.58 (doublet, J 9Hz PhCH-), 4.98 (doublet, J 4.5 Hz; C-6H), 5.19 (singlet; -CH$_2$CCl$_3$), 6.40, 6.75 (two doublets, J 18 Hzl C-2 H$_2$), and 8.00 (singlet, C-3 CH$_3$), on deuteration C-7 -CONH-, OCONH, -COOH collapsed and C-7H double doublet converted to a doublet (J 4.5 Hz) and PhCH= doublet converted to a singlet.

EXAMPLE 30 a. Bis Polymer Ester of (6R, 7R)-3-Hydroxymethyl - 7 (R-5-Trichloroethoxycarbonylamino-5-Carboxypentanamido) ceph-3-em-4-Carboxylic Acid 2,2,2-Trichloroethyl chloroformate (5 ml. 37 mm) was added to a solution of the potassium salt of desacetylcephalosporin C (20 mm) in water (100 ml). The solution pH was maintained at 7.5 - 8.0 for 30 minutes using 10% w/v sodium hydroxide solution. The solution was then extracted with dichloromethane at pH 5.0 the aqueous solution was extracted with ethylacetate (100 ml) at pH 2.5, then washed with a further aliquot of ethyl acetate (50 ml) the ethylacetate solution was dried over magnesium sulphate, concentrated to 80 ml and added to a slurry of polymer diazoalkane (8g, 20mm) (prepared as described above in the preparation of starting materials) in dichloromethane (100 ml) and dimethylformamide (10 ml). The mixture was stirred for 4 hours at ambient temperature, filtered, washed with ethyl acetate (2 × 25 ml) then dichloromethane (3 × 50 ml) and dried in vacuo to give 13.3.g product.

b. Bis Polymer Ester of (6R - 7R)-3-Trichloroacetylcarbamoyloxy methyl -7- (R5 - Trichloroethyloxycarbonylamino-5-Carboxypenta amido) ceph-3-em-4-Carboxylic Acid The polymer ester prepared in Example 30 (a) (13.1g) was stirred in dichloromethane (50 ml) at ambient temperature. Trichloroacetyl isocyanate (1.5 gm., 11.5 mm) was added and the mixture stirred for 30 minutes. The mixture was filtered, washed with dichloromethane (3 × 50 ml) and dried in vacuo to give 14.6 g product. Infra red spectroscopy indicated that the title cephalosporin was attached to the polymer beads.

c. Polymer Ester of (6R, 7R) -7-Amino-3-Trichloroacetylcarbamoyl-Oxymethylceph-3-em-4-Carboxylic Acid To a slurry of phosphorus pentachloride (6.5G, 31 mm) in dichloromethane (20 ml) was added pyridine (2.5.ml 31 mm) in dichloromethane (5 ml). The mixture was stirred for 15 minutes at + 15° then cooled −5°. A slurry of the product from reaction (30b) (14.5.g) in dichloromethane 75 ml) was added and the mixture stirred for 45 minutes at 15°, the mixture was cooled to −10°, methanol (35 ml) was added and the mixture stirred for 15 minutes at 15°, water (100 ml) was added and the mixture stirred for a further 10 minutes. After filtration, the product was washed with water (50 ml), methanol (2 × 50 ml) and dichloromethane (3 × 50 ml). After drying in vacuo 13.5.g product was obtained. IR and NMR spectra indicated that the title cephalosporin was attached to the polymer beads.

d. Polymer ester of (6R 7R) -7-Amino-3-Carbamoyloxymethyl ceph-3-em-4-Carboxylic Acid The product from reaction 30(c) (6.5g) was slurried with methanol (50 ml) and 10% w/v sodium bicarbonate solution (25 ml) added. The mixture was stirred for 2 hours at ambient temperature then filtered, washed with water (50 ml) methanol (2 × 50 ml) and dichloromethane (2 × 50 ml). After drying in vacuo 6.1 g product was obtained.

e. (6R, 7R)-7-Amino-3-carbamoyloxymethylceph-3-em-4-carboxylic acid

The product from reaction 30(D) (5.00F) was slurried with chloroform (50 ml. containing 2% V/V ethanol) and trifluoroacetic acid (25 ml). The mixture was stirred for 1 Hr. at room temperature then filtered. The polymer was washed with chloroform (4 × 50 ml) and dried in vacuo (3.71g). The combined chloroform filtrates were evaporated to dryness under reduced pressure at less than 25 DEG. water (35 ml) was added, the pH adjusted to 8.0 with 0.88 ammonia solution, and charcoal (0.5 g) added. After 30 min at room temperature, the mixture was filtered, and the filtrate adjusted to pH 2.5 with concentrated hydrochloric acid. The resulting oily precipitate was taken up in methyl isobutylketone (10 ml), and the mixture filtered. The solid was washed with methylisobutylketone (5 ml) and water (5 × 10 ml) and dried to constant weight in vacuo over P$_2$O$_5$ to give (6R, 7R)-7-amino-3-carbamoyloxymethyl-ceph-3-em-4-carboxylic acid (83.9 mg) which proved to be identical (IR, N.M.R., and T.L.C.) with an authentic sample.

EXAMPLE 31 a. Polymer ester of (6R 7R)-7-amino-3-chloromethyl ceph-3-em-4-carboxylic acid

A stirred suspension of the polymer bis ester of (6R, 7R)-3-hydroxymethyl-7-(R-5-trichloroethyloxycarbonylamino-5-carboxypentanamido-(ceph-3-em-4-carboxylic acid (7.4 g, 0.005 mole) containing 0.68 m.mole of cephalosporin moiety/g of polymer prepared as in Example 11, in methylene chloride (100 ml) at −15° under nitrogen was treated with phosphorus trichloride (0.70 g., 0.005 mole). After 15 min., phosphorus pentachloride (3.13 g, 0.015 mole) and dry pyridine (2.5 ml, 2.45 g, 0.031 mole) was added and the mixture stirred at −15° for 30 minutes and then for a further 30 minutes while allowing the temperature to rise from −15° to +15°. The dark brown reaction mixture was cooled to 0° and methanol (10 ml) was added maintaining the temperature at 0° to 5°. When addition was complete the stirred mixture was allowed to rise to room temperature when water (10 ml) was added. After stirring for 15 minutes the reaction mixture was filtered and the produce washed successively with methylene chloride (3 × 100 ml) methanol (2 × 100 ml) water (3 × 100 ml) methanol (2 × 100 ml) and methylene chloride (3 × 100 ml) and dried in vacuo at 30° to constant weight.

The polymer product 7.23 g) was orange in colour. A sample of the title polymer product on suspending in methylene chloride, spraying with a 0.5% solution of ninhydrin in butan-1-ol and warming gave a deep purple colouration indicative of the production of the title compound. The polymer ester of (6R 7R -3-hydroxy methyl-7(R-5-trichloroethyloxycarbonylamino-5-carboxypentanamido)-ceph-3-em-4-carboxylic acid gave under the same conditions, a negative test with ninhydrin. The diphenylmethyl ester of the title cephalosporin also gives a deep purple colour on spraying with ninhydrin.

b. Polymer ester of (6R - 7R)-3-chloromethyl-7-(2-thienylacetamido)ceph-3-em-4-carboxylic acid A suspension of the polymer ester of (6R, 7R)-7-amino-3-chloromethylceph-3-em-4-carboxylic acid. (5.00g, from example 31(a) was stirred in methylene chloride (100 ml) under nitrogen for 30 minutes at room temperature 18-21 degrees). The mixture was cooled to 0° and propylene oxide (1.74 g, 0.03 ml) was added, and stirring continued for 30 min. Thienylacetylchloride (3.0 ml. 3.89 g. 0.024 ml) was added dropwise over a period of 10 minutes maintaining the temperature 0°–5°. When the addition was completed, stirring was continued for 15 minutes at 0°–5° and then for a further 5 hours allowing the temperature to rise to room temperature. The reaction mixture was filtered and pulled as dry as possible. The product was washed in methylene chloride (3 × 40 ml), methanol (2 × 40 ml), water (4 × 40 ml) methanol (2 × 40 ml), and methylene chloride (3 × 40 ml) and dried to constant weight in vacuo at 30° to give the yellow-orange coloured polymer ester of (6R, 7R)-3-chloromethyl-7-(2-thienylacetamido) ceph-3-em-4-carboxylic acid (5.10 g). A sample of the product on suspending in methylene chloride, spraying with a 0.5% solution of ninhydrin in butan-1-ol, and warming gave an orange colouration indicating that the starting product had been consumed and the title product had been formed.

EXAMPLE 32

Polymer ester of penicillin G 1-oxide and polymer diazomethylene prepared from the hydrazone of benzoylated styrene-2% divinyl benzene copolymer A stirred slurry of the polymer diazomethylene (200–400 mesh, 5.0 g; 80 - 170 mesh, 5.0 g) prepared as described in Example 1(a), 1(b) and 1(c) of British Patent Application No. 36384/73 in chloroform (50 ml. containing 2% v/$_v$ ethanol) at room temperature was treated dropwise over 10 minutes with a solution of Penicillin G sulphoxide acid acetone solvate (8.0g; 1.958 × 10$^{-2}$ mole) in chloroform (50 ml. containing 2% v/$_v$ ethanol) in a closed apparatus. Reaction was immediate and the nitrogen evolved was collected by downward displacement of warer. Esterification was complete when the deep magneta colour had faded completely to a pale yellow colour, the nitrogen evolution having then ceased (200 - 400 mesh, 320 ml. nitrogen in 60 minutes; 80 - 170 mesh, 310 ml. nitrogen in 105 minutes). The mixture was stirred for a further 30 minutes and then filtered. The polymer ester was washed with chloroform (2 × 50 ml.) and dried in vacuo at 40° overnight. The products (200 - 400 mesh, 9.9g; 80 - 170 mesh, 9.86g) were pale yellow in colour. From the result of esterificaton the nitrogen content for the polymer diazomethylene products were: 200 - 400 mesh, 2.86 m.mole/g. of polymer; 80 - 170 mesh, 2.77 m. mole/g. of polymer.

EXAMPLE 33

Polymer ester of penicillin G 1-oxide and polymer diazomethylene prepared from the hydrazone of poly (benzoyl)

The polymer diazomethylene prepared as described in Example 5(a), 5(b), 5(c) and 5(d) of British Patent Application No. 36384/73 was treated with a solution of penicillin G sulphoxide acid acetone solvate in chloroform in a manner analogous to that described in Example 32. From the result of esterification the nitrogen valve of the polymer diazomethylene was 0.74 m.mole/g of polymer.

EXAMPLE 34

Polymer ester of penicillin G 1-oxide and polymer diazomethylene prepared from the hydrazone of poly(styrene-10% methylvinylketone)-2% divinylbenzene copolymer The polymer diazomethylene prepared so described in Examples 6(a), 6(b) and 6(c) of British Patent Application No. 36384/73 as a stirred slurry in chloroform (30 ml. containing 2% v/$_v$ ethanol at room temperature was treated dropwise over 1 minutes with a solution of Penicillin G sulphoxide acid acetone solvate (5.0g., 9.78 × 10$^{-2}$ mole) in chloroform (50 ml. containing 2% v/$_v$ ethanol) in a closed apparatus. Nitrogen )27ml.) was evolved over 15 minutes, the reaction mixture being stirred for a further 10 minutes. The polymer ester was filtered, washed with chloroform (2 × 50 ml.) and dried in vacuo at 40° overnight to give tee polymer ester (4.67g) as a white solid. The nitrogen evolved represents a nitrogen content of the title polymer diazomethylene of 0.29 m.mole/g. of polymer

EXAMPLE 35

Polymer Ester of (6R, 7R)-7 (D-2'-T-Butoxycarbonylamino-2'-Phenylacetamido)-3-Methylceph-3-em-4-Carboxylic acid To a stirred solution of methylchloroformate (0.6g, 6.37 mmol) in dried tetrahydrofuran (25ml) and dried methylene chloride (25ml) at 0° and under nitrogen was added dropwise over a period of 20 minutes a solution of N-(t-butoxycarbonyl)-d-α-phenylglycine (1.60g, 6.37 mmol), triethylamine (0.64g, 6.27 mmol) and N,N-dimethylaniline (6 drops) in dried tetrahydrofuran (25ml) and dried methylene chloride (25ml). After 30 minutes following the addition a suspension of the polymer ester of (6R,7R)-7-amino-3-methylceph-3-em-4-carboxylic acid (5.00g, 2.85mmol, from example 29 (c), triethylamine (0.30g, 2.97mmol) in dried tetrahydrofuran (25ml) and dried methylene chloride (25ml) was added over 10 minutes, and washed in with a few mls of methylene chloride. The mixture was stirred at 0°-5° for 2 hours and for a further 67 hours at room temperature. The reaction mixture was filtered, pulled as dry as possible and washed with methylene chloride (3 × 40ml), methanol (2 × 40ml), 5% w/v aqueous sodium hydrogen carbonate (2 × 40ml,) water (4 × 40ml), methanol (2 × 40ml), and methylene chloride (3 × 40ml), the product was dried to constant weight in vacuo at 35° to give the titled polymer ester as a yellow-brown coloured polymer (5.51g). t.l.c. (on silica gel and developed with butan-1-ol, glacial acetic acid, and water (5: 1: 4) of the product after cleavage with trifluoroacetic acid in methylene chloride indicated the presence of the trifluoroacetic acid salt of cephalexin (Rf 0.33) which proved to be identical with an authentic sample of cephalexin run under the same conditions. Absorption max (Nujol) 3350 (NH), 1782s (Beta-Lactam C=O) and 1695sb (C=O).

We claim:

1. An immobilised cephalosporin carboxylic acid derivative consisting essentially of a polymer containing recurring aromatic units having aliphatic carbon atoms attached to said recurring aromatic units and to a second aryl group, the said polymer carrying a plurality of molecules of a cephalosporin carboxylic acid, the carboxyl groups of which are directly bonded to said aliphatic carbon atoms by the formation of carboxylic acid ester linkages.

2. A derivative as claimed in claim 1 in which said second aryl group carries at least one substituent selected from the group consisting of halogen atoms, cyano groups, nitro groups, lower alkoxy groups and lower alkyl groups.

3. A derivative as claimed in claim 1 in which the polymer is a polymer of styrene, alpha-methyl styrene, or styrene and alpha-methyl styrene.

4. A derivative as claimed in claim 3 wherein said polymer is cross-linked with divinylbenzene.

5. A derivative as claimed in claim 1 in which each of said aliphatic carbon atoms forms part of a side chain attached to the backbone structure of the polymer or forms part of the backbone chain of the polymer.

6. A derivative as claimed in claim 3 in which at least 20% of the phenyl rings of the polymer carry cephalosporin carboxylate groups.

7. A derivative as claimed in claim 6 in which said cephalosporin carboxylate groups are attached to a methylene group one valency of which is attached to the polymer backbone chain through an arylene group and the other valency of which is attached to an aryl group.

8. A derivative as claimed in claim 7 wherein the arylene group is a phenylene group and the aryl group is phenyl, alkyl phenyl or alkoxyphenyl.

9. A derivative as claimed in claim 1 in which the polymer consists essentially of recurring units of the formula

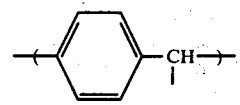

and

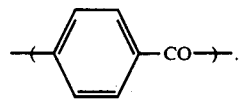

10. A derivative as claimed in claim 1 in which the polymer is in the form of a solid, particulate gel.

11. A derivative as claimed in claim 2 in which the cephalosporin acid is
(6R,7R)-3-methyl-7-phenylacetamidoceph-3-em-4-carboxylic acid;
(6R,7R)-7-amino-3-methylceph-3-em-4-carboxylic acid; and N-blocked (6R,7R)-3-methyl-7-(R-2-amino-2-phenylacetamido) ceph-3-em-4-carboxylic acid;
(1S,6R,7R)-3-methyl-7-phenylacetamidoceph-3-em-4-carboxylic acid 1-oxide;
N-blocked (6R,7R)-3-hydroxymethyl-7-(R-5-amino-5-carboxypentanamido) ceph-3-em-4-carboxylic acid;
(6R,7R)-3-methyl-7-(2-thienylacetamido)-ceph-3-em-4carboxylic acid;
(6R,7R)-7-amino-3-carbamoyloxymethyl-ceph-3-em-4-carboxylic acid;
(6R,7R)-7-amino-3-(N-blocked carbamoyloxymethyl)-ceph-3-em-4-carboxylic acid;
(6R,7R)-3-(N-blocked carbamoyloxymethyl)-7-(R-5-blocked amino-5-carboxypentanamido)-ceph-3-em-4-carboxylic acid;
(6R,7R)-7-amino-3-chloromethylceph-3-em-4-carboxylic acid;
(6R,7R)-7-(R-2-amino-2-phenylacetamido)-3-methylceph-3-em-4-carboxylic acid; or
(6R,7R)-3-chloromethyl-7-(2-thienylacetamido)ceph-3-em-4-carboxylic acid.

12. A derivative as claimed in claim 11 wherein N-blocking is effected by means of a 2,2,2-trichloroethoxycarbonyl of t-butoxycarbonyl group.

* * * * *